United States Patent
Kline

(10) Patent No.: US 7,547,285 B2
(45) Date of Patent: Jun. 16, 2009

(54) DEVICE AND METHOD FOR COLLECTION OF EXHALED ALVEOLAR BREATH CONDENSATE

(75) Inventor: Jeffrey A. Kline, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 512 days.

(21) Appl. No.: 10/778,477

(22) Filed: Feb. 13, 2004

(65) Prior Publication Data

US 2004/0162500 A1 Aug. 19, 2004

Related U.S. Application Data

(60) Provisional application No. 60/447,581, filed on Feb. 14, 2003.

(51) Int. Cl.
*A61B 5/08* (2006.01)
(52) U.S. Cl. ........................ 600/532; 600/529
(58) Field of Classification Search ......... 600/529–532; 73/23.3; 422/84
See application file for complete search history.

(56) References Cited

U.S. PATENT DOCUMENTS

| | | | | |
|---|---|---|---|---|
| 3,000,379 | A * | 9/1961 | Viers | 128/204.16 |
| 3,420,224 | A | 1/1969 | Farr | 128/2.07 |
| 3,613,665 | A | 10/1971 | Gorsuch | 128/2 R |
| 3,622,278 | A | 11/1971 | Elzinga et al. | 23/232 R |
| 3,830,630 | A | 8/1974 | Kiefer et al. | 23/232 E |
| 4,248,245 | A | 2/1981 | Kempin | 128/719 |
| 4,259,951 | A | 4/1981 | Chernack et al. | 128/200.14 |
| 4,322,217 | A | 3/1982 | Dikeman | 23/230 B |
| 4,349,626 | A | 9/1982 | Labows et al. | 435/38 |
| 4,370,413 | A | 1/1983 | Neeman et al. | 435/39 |

(Continued)

FOREIGN PATENT DOCUMENTS

EP  0 759 169 B1  1/1998

(Continued)

OTHER PUBLICATIONS

Kimura et al. "Alleviation of Monocrotaline-Induced Pulmonary Hypertension by Antibodies to Monocyte Chemotactic and Activating Factor/Monocyte Chemoattractant Protein-1," *Laboratory Investigation* 1998 78:571-81.

(Continued)

*Primary Examiner*—Patricia Mallari
*Assistant Examiner*—Karen E Toth
(74) *Attorney, Agent, or Firm*—K&L Gates LLP

(57) ABSTRACT

A diagnosis method for respiratory disease based on the separation of the expired airway phase in an exhaled breath from the alveolar phase, and a device to accomplish the method. The device includes a cartridge assembly and a disposable condensing chamber carried in a substantially enclosed housing. The cartridge assembly includes a disposable cartridge and a reusable control system that monitors a characteristic of gas passing through the cartridge to determine when to divert the exhaled breath to an exhaust outlet and when to divert the exhaled breath to the condensing chamber. The characteristic is selected as being representative of the transition from the expired airway phase to the alveolar phase. Also included are a refrigeration system, an auxiliary monitoring system for determining when a sufficient volume of gas has been produced, and a built-in analyzer.

6 Claims, 23 Drawing Sheets

U.S. PATENT DOCUMENTS

| | | | | |
|---|---|---|---|---|
| 4,438,209 | A | 3/1984 | Mosier | 436/542 |
| 4,491,660 | A | 1/1985 | Gendrich et al. | 536/32 |
| 4,510,241 | A | 4/1985 | Mills | 435/23 |
| 4,818,489 | A | 4/1989 | Gönner et al. | 422/84 |
| 5,042,501 | A | 8/1991 | Kenny et al. | 128/719 |
| 5,310,657 | A | 5/1994 | Berzofsky | 435/34 |
| 5,327,901 | A | 7/1994 | Delente | 128/730 |
| 5,356,778 | A | 10/1994 | Hansen et al. | 435/7.2 |
| 5,376,555 | A | 12/1994 | Forrester et al. | 436/132 |
| 5,383,469 | A | 1/1995 | Vreman et al. | 128/719 |
| 5,465,728 | A | 11/1995 | Phillips | 128/730 |
| 5,487,380 | A | 1/1996 | Grabenkort | 128/204.15 |
| 5,501,212 | A | 3/1996 | Psaros | 128/205.12 |
| 5,541,057 | A | 7/1996 | Bogart et al. | 435/5 |
| 5,558,087 | A | 9/1996 | Psaros et al. | 128/205.12 |
| 5,634,517 | A | 6/1997 | Linden et al. | 165/111 |
| 5,655,526 | A | 8/1997 | Gibertoni | 128/205.27 |
| 5,702,882 | A | 12/1997 | Tamura et al. | 435/4 |
| 5,759,858 | A | 6/1998 | Nieuwenhuizen | 436/16 |
| 5,787,885 | A * | 8/1998 | Lemelson | 600/309 |
| 5,795,787 | A | 8/1998 | Silkoff et al. | 436/116 |
| 5,826,575 | A | 10/1998 | Lall | 128/205.12 |
| 5,876,947 | A | 3/1999 | Kudryk et al. | 435/7.1 |
| 5,938,637 | A | 8/1999 | Austin et al. | 604/72 |
| 5,998,389 | A | 12/1999 | Loverock | 514/54 |
| 6,010,459 | A | 1/2000 | Silkoff et al. | 600/532 |
| 6,033,368 | A | 3/2000 | Gaston, IV et al. | 600/532 |
| 6,132,610 | A | 10/2000 | Hirai et al. | 210/264 |
| 6,148,657 | A | 11/2000 | Satoh et al. | 73/23.35 |
| 6,149,603 | A | 11/2000 | Parker | 600/532 |
| 6,186,958 | B1 | 2/2001 | Katzman et al. | 600/532 |
| 6,221,026 | B1 | 4/2001 | Phillips | 600/532 |
| 6,283,122 | B1 | 9/2001 | Adahan | 128/205.24 |
| 6,312,390 | B1 | 11/2001 | Phillips | 600/532 |
| 6,341,520 | B1 | 1/2002 | Satoh et al. | 73/23.35 |
| 6,363,772 | B1 | 4/2002 | Berry | 73/24.02 |
| 6,384,188 | B1 | 5/2002 | Hoess et al. | 530/326 |
| 6,419,634 | B1 | 7/2002 | Gaston, IV et al. | 600/532 |
| 6,491,643 | B2 | 12/2002 | Katzman et al. | 600/532 |
| 6,582,376 | B2 | 6/2003 | Baghdassarian | 600/543 |
| 6,585,661 | B1 | 7/2003 | Hunt et al. | 600/532 |
| 6,612,306 | B1 * | 9/2003 | Mault | 128/204.22 |
| 6,645,724 | B1 | 11/2003 | Ding et al. | 437/7.1 |
| 6,656,127 | B1 | 12/2003 | Ben-Oren et al. | 600/532 |
| 6,726,637 | B2 * | 4/2004 | Phillips | 600/543 |
| 6,824,520 | B2 * | 11/2004 | Orr et al. | 600/529 |
| 7,118,537 | B2 * | 10/2006 | Baddour | 600/543 |
| 2001/0021815 | A1 | 9/2001 | Katzman et al. | 600/532 |
| 2003/0050567 | A1 * | 3/2003 | Baghdassarian | 600/543 |
| 2003/0208132 | A1 | 11/2003 | Baddour | 600/543 |
| 2004/0138577 | A1 | 7/2004 | Kline | 600/543 |
| 2004/0162500 | A1 | 8/2004 | Kline | 600/532 |
| 2004/0234971 | A1 | 11/2004 | Jackman | 435/6 |
| 2005/0208614 | A1 | 9/2005 | Kline | 435/34 |

FOREIGN PATENT DOCUMENTS

| | | |
|---|---|---|
| WO | WO 01/84112 A1 | 11/2001 |
| WO | WO 02/082977 A2 | 10/2002 |
| WO | WO 2006/007180 A2 | 1/2006 |

OTHER PUBLICATIONS

Ikeda et al., "Anti-monocyte chemoattractant protein-1 gene therapy attenuates pulmonary hypertension in rats," *Am J Physiol Heart Circ Physiol*, 2002, 283(5):H2028.

Sergei A. Kharitonov and Peter J. Barnes, "Exhaled Markers of Pulmonary Disease", *American Journal of Respiratory and Critical Care Medicine*, vol. 163, pp. 1693-1722, 2001.

George Nakos, Eirene I. Kitsiouli and Marilena E. Lekka, "Bronchoalveolar Lavage Alterations in Pulmonary Embolism", *American Journal of Repiratory and Critical Care Medicine*, vol. 158, pp. 1504-1510, 1998.

U.S. Appl. No. 60/434,916, filed Dec. 20, 2002, Kline.

Matthias Griese, Jochen Noss, Christina von Bredow, "Protein Pattern of Exhaled Breath Condensate and Saliva", *Proteomics* 2002, 2, pp. 690-696.

International Search Report, PCT/US04/04321, International Filing Date Feb. 13, 2004.

International Search Report, PCT/US05/18232, International Filing Date May 24, 2005.

*National Hospital Ambulatory Medical Care Survey: 2002 Emergency Department Summary*, Linda F. McCaig et al., Division of Health Care Statistics, U.S. Department Of Health and Human Services, No. 340, Mar. 18, 2004, pp. 1-35.

*A Rapid Qualitative Assay to Detect Circulating Endotoxin Can Predict the Development of Multiorgan Dysfunction*, M.H. Kollef et al, Chest, vol. 112,173-180, © 1997 by American College of Chest Physicians, http://www.chestjournal.org/cgi/content/abstract/112/1/173, May 21, 2004, 1 page.

*Untersuchungen zur Anwendbarkeit der Atemkondensatgewinnung beim Pferd und ihre Potentiellen Einsatzmöglichkeiten in der Lungendiagnostik*, Sandra Schack, Abstract, http://bibd.uni-giessen.de/ghtm/2002/uni/d020068b.htm, Nov. 19, 2002, 1 page.

*Total Nitrite/Nitrate in Expired Breath Condensate of Patients With Asthma*, K. Ganas et al., PNEUMON, http://www.mednet.gr/pneumon/1403-6e.htm, Nov. 19, 2002, 1 page.

U.S. Appl. No. 10/742,721, filed Dec. 19, 2003, Kline.

*Breath Condensate: Rich Source of Exhaled Markers and Mediators. Methodological Issues and Standardisation of Measurements*, Kharitonov et al., National Heart and Lung Institute, Imperial College, Dovehouse Street, London SW3 6LY, UK, www.filt.de/Hauptmenue/Aktuelles_Current_Affairs/Page10464/Breath/_Condensate, Nov. 19, 2002, 2 pages.

*Mycobacterium Tuberculosis Gene-Amplification in Breath Condensate of Patients with Lung Tuberculosis*, J. Schreiber et al., European Journal of Medical Research, Jun. 28, 2002, pp. 290-291.

*Expired Hydrogen Peroxide in Breath Condensate of Cystic Fibrosis Patients*, L.P. Ho et al., Abstract, Eur Respir J 1999; 13:103-106, http://www.personal.u-net.com/, Nov. 19, 2002.

*Meeting Report—World Congress on Lung Health and 10th ERS Annual Congress* Aug. 30- Sep. 3, 2000, Florence, Italy, Pieter S. Hiemstra, Respir Res 2000, 1:178-179, http://resiratory-research.com/content/1/3/178.

*Breath Condensate*, info Special Edition, 1st Edition, Apr. 2001, Jaeger a subsidiary of VIASYS Healthcare, Hoechberg, Germany, pp. 1-28.

*Diagnosis of Gram Negative, Ventilator Associated Pneumonia by Assaying Endotoxin in Bronchial Lavage Fluid*, P.G. Flanagan et al., J. Clin Pathol 2001:54:107-110, Mar. 16, 2005; www.jcp.bmj-journals.com.

*Rapid Diagnosis of Gram Negative Pneumonia by Assay of Endotoxin in Bronchoalveolar Lavage Fluid*, Jerome Pugin et al. Thorax 1992: 47:547-549.

*Pseudomonas aeruginosa and Burkholderia cepacia Cannot Be Detected by PCR in the Breath Condensate of Patients With Cystic Fibrosis*, Vogelberg, C., et al.; Pediatric Pulmonology 36:348-352 (2003).

U.S. Appl. No. 10/884,179, filed Jul. 4, 2004, Kline.
U.S. Appl. No. 11/071,745, filed Mar. 3, 2005, Kline.
U.S. Appl. No. 11/605,727, filed Nov. 29, 2006, Kline.
U.S. Appl. No. 11/605,872, filed Nov. 29, 2006, Kline.
U.S. Appl. No. 11/799,176, filed May 1, 2007, Kline.
PCT/US03/41209, filed Dec. 19, 2003, Kline.
PCT/US05/006908, filed Mar. 3, 2005, Kline.
PCT/US06/19911, filed May 23, 2006, Kline.
Supplemental European Search Report.

* cited by examiner

DEVICE AND METHOD FOR COLLECTION OF EXHALED ALVEOLAR BREATH CONDENSATE

CROSS-REFERENCE TO RELATED APPLICATION

This application is entitled to the benefit of, and claims priority to, provisional U.S. patent application Ser. No. 60/447,581 filed Feb. 14, 2003 and entitled "DEVICE AND METHOD FOR COLLECTION OF EXHALED ALVEOLAR BREATH CONDENSATE," the entirety of which is incorporated herein by reference.

BACKGROUND OF THE PRESENT INVENTION

1. Field of the Present Invention

The present invention relates generally to breath condensate collection, and more particularly, to full-featured breath condensate collection apparatuses capable of separating the expired airway phase of mammalian exhalation from the alveolar phase.

2. Background

As is well known, exhaled breath condensate contains water-soluble and water insoluble molecules, including dissolved gases, organic solutes, ions and proteins. Analysis of the molecular content of breath condensate can provide a method to diagnose and prognose certain diseases. (S. A. Kharitonov and P. J. Barnes, Exhaled markers of pulmonary disease, *Am J Respir Crit Care Med* 163:1693-1722, 2001.) However, the measurement of substances in exhaled condensate as a method to determine the presence of pathophysiologic processes in the lung alveoli is degraded by contamination by substances arising from the mouth, nose, throat and the tracheobronchial tree. Using two dimensional gel electrophoresis, Griese and colleagues demonstrated distinctly different proteins in breath condensate collected from oral breathing, compared with nasal breathing (M. Griese, *Proteomics* 2:690-696, 2002.) This contamination can cause false positive testing.

It is our hypothesis that a gating mechanism can be triggered from the measurement of the partial pressure of carbon dioxide in exhaled breath to open and close during the exhalation cycle in a manner to separate out the contaminant breath volume, generated during the expired airway phase of the exhalation cycle, from the alveolar volume generated during the alveolar phase of the cycle. The ability to selectively collect alveolar breath condensate rapidly and easily with a point-of-care device would improve the clinical utility of breath-based diagnosis for this purpose, particularly in the emergency department or clinic setting. The device described is designed to allow a patient to breath into a handheld disposable chamber to facilitate the collection of breath water vapor which can then be analyzed for biochemicals to detect the presence of specific diseases, including bacterial, chlamydial, mycoplasma, or fungal pulmonary infection, pulmonary embolism, pulmonary ischemia, systemic gram negative sepsis, fat embolism from sickle cell disease or after surgical fixation of fractures, carcinoma of the lung, asthmatic inflammation, and chronic obstructive pulmonary disease.

Experimental History and Observations Leading to Conception of Invention

An experimental pulmonary vascular occlusion (PVO), induced by venous infusion of polystyrene microspheres in rats, has been used to determine three major findings related to the device of the present invention. Using anesthetized, tracheostomized mechanically ventilated rats, exhaled-breath condensate was collected in a pilot version of the present invention. The condensing chamber consisted of a sterile pipette within dry ice. As compared with control rats, increased concentrations of proteins, eicosinoid derivatives and peptides associated with fibrinolysis were found in the condensate of rats with PVO. (Nakos, Am J Resp Crit Care Med 1998, 158:1504.) The magnitude of the concentration of these vasoconstrictive agents correlated with the severity of hypoxemia and pulmonary hypertension in the subject rats.

A variety of methods and apparatuses have been proposed for use in breath analysis, but none accomplish the needs and benefits of the present invention. Several of these, including U.S. Pat. Nos. 6,033,368 and 6,419,634 to Gaston et al., U.S. Pat. No. 6,585,661 to Hunt et al., U.S. Publication No. 2003/0208132 A1 to Baddour, Eur. Patent No. 0,759,169 B1 to Winsel et al., and PCT Patent App. No. 02/082977 to Vaughan et al., disclose breath condensate collection devices, but each has significant shortcomings. First, no known apparatus includes the use of a monitoring system in a breath condensate collection device as a mechanism to trigger a valve open and shut during the exhalation cycle for the purpose of collecting only one type of condensate—i.e., alveolar condensate or expired airway condensate. The former type of condensate is especially important in the use of a breath collection device to diagnose lower tract pulmonary infection, as it is necessary to eliminate contamination of the breath sample from the nasopharyngeal flora. Similarly, the latter type of condensate is especially important in diagnosing upper tract infection.

Other devices or methods are known for separating the expired airway phase from the alveolar phase for such purposes as the detection of alcohol levels in a person's breath. For example, U.S. Pat. No. 3,613,665 to Gorsuch, U.S. Pat. No. 3,830,630 to Kiefer, U.S. Pat. No. 4,248,245 to Kempin, U.S. Pat. No. 5,327,901 to Delente, U.S. Pat. No. 5,376,555 to Forrester disclose methods and apparatuses for achieving such separation. Some, but not all, of these devices and methods use active mechanisms for providing such separation, while others use passive means. Unfortunately, all known devices and methods suffer drawbacks. For example, the Gorsuch device measures temperature with a heated thermistor and triggers a valve when the temperature differential indicates that the alveolar phase has been reached, while the Kempin device measures temperature differentials to determine when to divert exhaled breath into a measuring chamber. Temperature-based valve triggers may not be as reliable as desired. Neither the Kiefer device nor the methodology disclosed by Forrester is used to physically separate the alveolar phase breath from expired airway phase breath. Instead, the filament used in Kiefer is used merely to activate an alcohol-measuring section, while the Forrester methodology uses automated analysis of infrared profiles of the exhaled breath to identify the different phases thereof. Finally, the Delente device is passive, relying on a simple technique to retain in a collection chamber only the last portion of an exhaled breath, which is assumed to be alveolar phase rather than expired airway phase because it comes from the end of the exhaled breath. None of these devices or methods are thus suitable for use in breath condensate collection.

Moreover, none of the known devices or methods for separating the expired airway phase from the alveolar phase have been applied to breath condensate collection devices. In fact, some of the devices, such as the Kempin device, takes steps or include features specifically to avoid condensation because it interferes with the measurement of the gases themselves.

Finally, although the Forrester methodology uses infrared analysis of exhaled breath, none of the devices or methods use spectrometry methods to determine when the alveolar phase of an exhaled breath has been reached and to trigger a valve creating physical separation of the alveolar phase from the expired airway phase.

A need exists for a specific condensation chamber designed to allow delivery of a sample of condensate to an analysis system that is separate from the machine in order to allow point-of-care immunoassay for certain antigens. In particular, a need exists for an immunoassay in the form of a small plastic cartridge, similar to a conventional home pregnancy test kit except that the antibodies in the matrix are directed against antigens that will help diagnose pulmonary embolism and pulmonary infection. Antibodies that will preferably be tested may include, but are not limited to, fibrinopeptide A, d-dimer, thromboxane (and its metabolites), leukotrienes, chemokines, interleukins, and bacterial, chlamydial, viral and mycoplasma antigens. Although the general intent of methodologies such as those disclosed in the Baddour and Vaughn patents may be somewhat similar to some of the purposes of the present invention, they fail to provide an apparatus for collecting condensate and then injecting approximately 50-500 µL of condensate from a tip into the immunoassay kit. In addition, a need exists for a device from which the condensate sample may be delivered to an arterial blood gas machine for analysis of pH, $pCO_2$, $pO_2$, lactate, urea, glucose and electrolytes.

The Baddour device is designed to collect exhaled breath condensate from patients with asthma. The Baddour device does not describe a plunger that extrudes the sample, but describes a "duckbill" valve that appears to be an internal chamber for sample collection. This must be removed and requires additional steps before the sample can be analyzed. Baddour fails to disclose a tip which can be used to dispense the condensate onto the immunoassay filter, and fails to disclose a system of snaps to lock the handle of the plunger in its "closed" position. All of these features are very useful in facilitating simple breath condensate collection and analysis. Neither the specific objective of injecting the sample onto a port of an immunoassay, nor the objective of being able to use the condenser as a delivery unit to perform point-of-care pH, gas tension, lactate and urea measurements can be done with either the Baddour or Vaughn device.

Although the Vaughn device appears to propose the use of an endothermic reaction to cool a condensing chamber, it does not disclose a means of packaging the reaction to make it easy to use at the patient's bedside. The Vaughn device also requires a complicated methodology for expressing collected condensate from a side port of the condensing chamber. A need exists for a simpler methodology.

No prior art device uses a flow transducer to indicate when an adequate volume of breath has been collected, or provides visual or aural feedback as to the rate and completion percentage. A device having such features would be much more convenient to use than prior art devices.

Further, no prior art device uses a high efficiency, miniature refrigeration unit, disposed within the breath collection device itself, to cool the breath condenser. Such a system would allow a new condensing chamber to be cooled rapidly without storing the chamber beforehand in a freezer and without resorting to means such as an endothermic reaction to provide a cooling effect.

A need exists for a full-featured breath condensate collection apparatus for separating alveolar phase exhaled breath from expired airway phase exhaled breath, having improved cooling features, a housing that substantially encloses the various components in order to protect them, to protect the user from uncomfortable heat or cold produced thereby, to avoid contamination to or from the components, to provide greater convenience of use to the user, and to provide built-in analysis of the condensate collected therein.

SUMMARY OF THE PRESENT INVENTION

The device is designed to allow selective collection of breath condensate contained within the alveolar volume of expired breath. The device consists of port into which a patient breathes, connected in fluid series to a chamber with a port to allow transmission and measurement of percentage absorption of a light beam in the exhaled sample. In a preferred embodiment, when the concentration of $CO_2$ increases above a specified threshold, or increases at a specified rate, a rotary solenoid is actuated which is connected to a valve. This action causes the valve to rotate 90°, causing the exhaled breath to be diverted into a condensing chamber.

Other general features include a built-in refrigeration system, a built-in analyzer, a flow transducer and microcontroller for measuring total volume of exhaled breath and signaling the user when a sufficient volume has been detected, and a housing in which the various components may be carried, including some disposable components and some reusable components.

Broadly defined, the present invention according to one aspect is a method of diagnosing particular diseases based on expired breath from a mammalian subject, including: providing a breath condensate collection device having condensing chamber, a fluid inlet and a fluid outlet; cooling the condensing chamber; receiving, at the fluid inlet, at least one exhaled breath from a mammalian subject; separating the exhaled breath into an expired airway phase volume and an alveolar phase volume; condensing portions of either the expired airway phase portion of the exhaled breath or the alveolar phase volume of the exhaled breath, but not both, in the condensing chamber to produce condensate on the inner surfaces of the condensing chamber; removing the condensate from the condensing chamber; analyzing the condensate for markers indicative of respiratory disease; and rendering a diagnosis at least partly on the basis of whether the condensate being analyzed came, from the expired airway phase portion of the exhaled breath or the alveolar phase volume of the exhaled breath.

In features of this aspect, the separating takes place between the fluid inlet and the condensing chamber; the markers include biochemicals; the biochemicals include inorganic gases, volatile organic molecules, proteins, nucleic acids, lipids, lipid A, endotoxin and other impervious nonorganic exogenous materials; the markers include microbes; the microbes include viruses, fungi, mycoplasma, mycobacteria, bacteria, prions and protozoa; only the alveolar phase volume of the exhaled breath reaches the condensing chamber; alternatively, only the expired airway phase volume of the exhaled breath reaches the condensing chamber; the receiving, separating and condensing steps are repeated in order to increase the amount of condensate produced in the condensing chamber; and the method further includes expressing the condensate from the condensing chamber using a piston assembly.

Broadly defined, the present invention according to another aspect is a method of collecting breath condensate from a portion of exhaled breath from a mammalian subject by separating the expired airway phase of the breath from the alveolar phase, including: providing a cartridge assembly and a condensing chamber, the cartridge assembly having a breathing port and at least two fluid outlets, at least one of which is in fluid communication with the condensing chamber; cooling the condensing chamber; receiving, at the breathing port in the cartridge assembly, at least one exhaled breath from a mammalian subject; monitoring, in the cartridge assembly, at least one characteristic of the exhaled breath, the characteristic generally capable of distinguishing the expired airway phase of the breath from the alveolar phase of the breath; based on the state of the monitored characteristic, diverting the flow of the exhaled breath through the cartridge assembly from one fluid outlet to the other fluid outlet; and upon receiving a diverted portion of the exhaled breath from the cartridge assembly, condensing portions of the exhaled breath to produce condensate on the inner surfaces of the condensing chamber.

In features of this aspect, monitoring includes determining when the exhaled breath has transitioned from the expired airway phase to the alveolar phase, and diverting the flow of the exhaled breath based on the state of the monitored characteristic includes diverting the exhaled breath to the condensing chamber once it is determined that the alveolar phase of the exhaled breath has begun; cooling the condensing chamber includes cooling the condensing chamber to a temperature of less than 0° F.; the diverting step includes adjusting the state of a valve assembly to prevent the exhaled breath from passing into the condensing chamber until the alveolar phase of the exhaled breath has begun and to force the exhaled breath into the condensing chamber once the alveolar phase of the exhaled breath has begun; cooling the condensing chamber includes cooling the condensing chamber to a temperature of less than 0° C.; and the method further includes expressing the condensate from the condensing chamber using a piston assembly.

In other features of this aspect, determining when the exhaled breath has transitioned from the expired airway phase to the alveolar phase includes determining when a predetermined level of a particular predetermined gas is reached; the particular predetermined gas is selected from the group consisting of $CO_2$, $O_2$, $N_2$, CO and NO; the monitoring, diverting and condensing steps are repeated in order to increase the amount of condensate produced in the condensing chamber; the monitoring, diverting and condensing steps are repeated for a predetermined period of time; the monitoring, diverting and condensing steps are repeated until a predetermined volume of gas has passed into the condensing chamber; the monitoring and diverting steps are carried out automatically; and monitoring includes determining when the exhaled breath has transitioned from the expired airway phase to the alveolar phase, and diverting the flow of the exhaled breath based on the state of the monitored characteristic includes diverting the exhaled breath to the condensing chamber until it is determined that the alveolar phase of the exhaled breath has begun.

Broadly defined, the present invention according to another aspect is breath condensate collection apparatus including: a cartridge assembly having a breathing port adapted to permit a mammalian subject to breathe in and out of the cartridge assembly, at least a first fluid outlet and a second fluid outlet, a monitoring system adapted to monitor at least one characteristic of a generally gaseous fluid passing through the cartridge assembly, the at least one characteristic generally capable of distinguishing the expired airway phase of an exhaled breath from the mammalian subject from the alveolar phase of the exhaled breath, and a valve assembly operable to divert the flow of fluid, received via the breathing port, to either the first fluid outlet or the second fluid outlet on the basis of the state of the monitored characteristic; and a condensing chamber having double'side walls, including an inner side wall and an outer side wall in spaced relationship to one another, and first and second opposing ends, the condensing chamber being in fluid communication with at least one fluid outlet of the cartridge assembly.

In features of this aspect, the condensing chamber includes an outlet and a one-way valve adapted to prevent gas from being drawn into the condensing chamber during an inhalation by the mammalian subject while permitting exhaled breath to be exhausted therethrough during an exhalation by the mammalian subject; the condensing chamber is cooled to a temperature of less than 0° F.; the condensing chamber is cooled to a temperature of less than 0° C.; the apparatus further includes a plunger assembly having a piston and a handle, the piston being slidably disposed in the interior of the condensing chamber in snug contact with the inner side wall and the handle extending from the first end of the condensing chamber so as to permit the piston to be moved within the central chamber; and in addition to the first one-way valve, the cartridge assembly further includes an inhalation port and a second one-way valve adapted to permit breathing gas to be drawn into the cartridge assembly during an inhalation by the mammalian subject, and the cartridge assembly further includes a third one-way valve in at least one of the at least two fluid outlets adapted to prevent gas from being drawn into the cartridge assembly during an inhalation by the mammalian subject while permitting exhaled breath to be exhausted therethrough during an exhalation by the mammalian subject.

In other features of this aspect, the actuator device operates the valve assembly to divert the flow of fluid, received via the breathing port, to the second fluid outlet instead of to the first fluid outlet when a predetermined level of a particular predetermined gas is reached; the predetermined level is reached by the level of the predetermined gas rising to the predetermined level; the predetermined level is reached by the level of the predetermined gas dropping to the predetermined level; the particular predetermined gas is selected from the group consisting of $CO_2$, $O_2$, $N_2$, CO and NO; the breathing port, the at least two fluid outlets and the valve assembly define a cartridge, and the apparatus further includes a housing adapted to carry the cartridge, the monitoring system and the condensing chamber; and the cartridge is adapted to be removable from the housing for disposal after a single use, while the monitoring system is adapted for repeated reuse.

In still further features of this aspect, the actuator device operates the valve assembly to divert the flow of fluid, received via the breathing port, to the fluid outlet connected to the condensing chamber when the predetermined level of the particular. predetermined gas is reached; the actuator device operates the valve assembly to divert the flow of fluid, received via the breathing port, away from the fluid outlet connected to the condensing chamber when the predetermined level of the particular predetermined gas is reached; the valve assembly includes a valve adjustable between at least two positions, such that in the first valve assembly state the valve is in a first position diverting fluid received at the breathing port to the first fluid outlet and away from the second fluid outlet, and in the second valve assembly state the valve is in a second position diverting fluid received at the breathing port to the second fluid outlet and away from the first fluid outlet; the valve is a directional flap; the actuator device is a rotary solenoid; and the valve assembly includes at least two valves.

Broadly defined, the present invention according to another aspect is an apparatus for separating the expired airway phase of breath exhaled by a mammalian subject from the alveolar phase of the exhaled breath, including: a fluid inlet; at least a first fluid outlet and a second fluid outlet; a valve assembly adjustable between at least two states: a first state wherein fluid received at the fluid inlet is diverted to the first fluid outlet, and a second state wherein fluid received at the fluid inlet is diverted to the second fluid outlet; and a control system that adjusts the state of the valve assembly, having a spectrometer arranged to monitor at least one characteristic of a generally gaseous fluid passing through the separation apparatus, the characteristic generally capable of distinguishing the expired airway phase of an exhaled breath from a mammalian subject from the alveolar phase of the exhaled breath, and an actuator device, coupled to the spectrometer and the valve assembly, that adjusts the state of the valve assembly on the basis of the state of the monitored characteristic.

In features of this aspect, the spectrometer is arranged to measure the partial pressure of a particular predetermined gas in the gaseous fluid passing through the separation apparatus; the actuator device adjusts the state of the valve assembly from its first state to its second state when the partial pressure of the particular predetermined gas reaches a predetermined level; the partial pressure reaches the predetermined level by rising to the predetermined level; the partial pressure reaches the predetermined level by dropping to the predetermined level; the particular predetermined gas is selected from the group consisting of $CO_2$, $O_2$, $N_2$, CO and NO; the fluid inlet, the at least two fluid outlets and the valve assembly define a cartridge assembly, and the apparatus further includes a housing adapted to carry the cartridge assembly and the control system; and the cartridge assembly is adapted to be removable from the housing for disposal after a single use, while the control system is adapted for repeated reuse.

In other features of this aspect, the apparatus further includes a chamber having an inlet connected in fluid communication with one of the at least two fluid outlets and adapted to collect at least a portion of the generally gaseous fluid passing through the separation apparatus; the chamber is a condensing chamber adapted to collect liquid condensed out of the generally gaseous fluid; the chamber is connected to the second fluid outlet, and the actuator device adjusts the valve assembly from the first state to the second state when the partial pressure reaches the predetermined level; the chamber is connected to the second fluid outlet, and the actuator device adjusts the valve assembly from the second state to the first state when the partial pressure reaches the predetermined level; the valve assembly includes a valve adjustable between at least two positions such that in the first valve assembly state the valve is in a first position diverting fluid received at the fluid inlet to the first fluid outlet and away from the second fluid outlet, and in the second valve assembly state the valve is in a second position diverting fluid received at the fluid inlet to the second fluid outlet and away from the first fluid outlet; the valve is a directional flap; the actuator device is a rotary solenoid; and the valve assembly includes at least two valves.

Broadly defined, the present invention according to another aspect is a breath condensate collection apparatus including: a housing; a condensing chamber, carried by the housing, having an inlet that receives exhaled breaths from a mammalian subject and an outlet that permits a gaseous, non-condensed portion of the exhaled breaths to escape from the condensing chamber; and a built-in refrigeration system, carried by the housing, having a compressor, an expansion valve, an evaporator pipe arranged to cool the condensing chamber, and a condenser-pipe arranged to dissipate heat away from the condensing chamber.

In features of this aspect, the housing includes a cavity correspondingly shaped and sized to carry the condensing chamber, and the evaporator pipe is disposed generally around the cavity; when the condensing chamber is carried in the cavity, the condensing chamber makes contact with a substantial portion of the evaporator pipe; the condensing chamber has walls constructed from a good heat conducting material; the walls of the condensing chamber are constructed from aluminum; the apparatus further includes a ventilation system that dissipates heat generated by the refrigeration system; the ventilation system includes one or more vents in the housing; the ventilation system includes one or more fans; and the apparatus further includes a temperature gauge arranged to provide an indication of the temperature of the condensing chamber.

Broadly defined, the present invention according to another aspect is a portable breath condensate collection apparatus including: a housing having at least one compartment adapted to receive and generally enclose a removable cartridge and a removable condensing chamber in fluid communication with one another; a removable, disposable cartridge, having at least one inlet, at least one outlet and a mouthpiece in fluid communication with at least one inlet, carried in the at least one compartment of the housing such that at least a portion of the mouthpiece is carried externally to the housing; and a removable condensing chamber, having an inlet and an outlet, carried in the at least one compartment of the housing such that the inlet is in fluid communication with at least one outlet of the cartridge and the outlet is open to the environment.

In features of this aspect, the at least one compartment includes a compartment having a first section and a second section, the cartridge is carried in the first compartment section and the condensing chamber is carried in the second compartment section; alternatively, the at least one compartment includes at least a first compartment and a second compartment, the cartridge is carried in the first compartment and the condensing chamber is carried in the second compartment; the cartridge includes a valve assembly for alternately permitting or preventing the flow of fluids through the cartridge and into the condensing chamber; the apparatus further includes a control system, carried by and generally enclosed in the housing, for the valve assembly; and the control system is adapted to remain in the housing for repeated reuse while the cartridge and the condensing chamber are removed.

In other features of this aspect, the apparatus further includes an analyzer, carried by and generally enclosed in the housing, adapted to provide information regarding the content of breath condensate received therein, and a conduit disposed in sealed fluid communication between the condensing chamber and the analyzer, adapted to guide breathe condensate from the condensing chamber to the analyzer; wherein the condensing chamber further includes a piston and a handle, the piston is slidably disposed in the interior of the condensing chamber in snug contact with the inside of the condensing chamber and the handle extends from the first end of the condensing chamber so as to permit the piston to be moved within the central chamber; and the piston is operable to force breath condensate collected in the condensing chamber to the conduit leading to the analyzer.

Broadly defined, the present invention according to another aspect is a breath condensate collection apparatus including: a housing; a condensing chamber, carried by the housing; an inlet, carried by the housing, that receives exhaled breath from a mammalian subject; a conduit disposed in sealed fluid communication between the inlet and the condensing chamber; a gas flow measurement device, disposed in the conduit, that measures the flow of gas through the conduit; and a control system, coupled to the gas flow measurement device, that determines when a predetermined volume of gas has passed through the conduit.

In features of this aspect, the conduit, the gas flow measurement device and the control system are carried by the housing; the apparatus further includes a signaling device that generates a user-identifiable indication that the predetermined volume of gas has passed through the conduit; the gas flow measurement device is a gas flow transducer and the control system includes a microcontroller that is electrically connected to the gas flow transducer; the signaling device includes a speaker that generates a user-audible signal; the user-audible signal changes, as a mammalian subject breathes through the apparatus, to provide an indication of progress toward reaching the predetermined volume of gas; the signaling device includes at least one user-visible light; and the at least one user-visible light includes a plurality of user-visible lights that light sequentially, as a mammalian subject breathes through the apparatus, to provide an indication of progress toward reaching the predetermined volume of gas.

Broadly defined, the present invention according to another aspect is a breath condensate collection apparatus for separating the expired airway phase of breath exhaled by a mammalian subject from the alveolar phase of the exhaled breath, including: a housing; a cartridge assembly having a breathing port, at least two fluid outlets, a valve assembly adjustable between at least two states, including a first state wherein gas received at the breathing port is diverted to a first of the at least two fluid outlets, and a second state wherein gas received at the breathing port is diverted to a second of the at least two fluid outlets, a monitoring system arranged to monitor at least one characteristic of gas passing through the separation apparatus, the characteristic generally capable of distinguishing the expired airway phase of an exhaled breath from a mammalian subject from the alveolar phase of the exhaled breath, and an actuator device, coupled to the monitoring system and the valve assembly, that adjusts the valve assembly state on the basis of the state of the monitored characteristic; a condensing chamber, having an inlet and an outlet, carried by the housing such that the inlet is in fluid communication with at least one outlet of the cartridge assembly and the outlet is open to the environment; and a built-in refrigeration system, carried by the housing.

In features of this aspect, the housing includes at least one compartment adapted to receive and generally enclose the cartridge assembly and the condensing chamber in fluid communication with one another; the condensing chamber is adapted to be removed from the housing after use and replaced by a previously-unused condensing chamber; the cartridge assembly is adapted to be removed from the housing after use and replaced by an unused cartridge assembly; the condensing chamber has double side walls and first and second opposing ends, and the double side walls include an inner side wall and an outer side wall in spaced relationship to one another; the built-in refrigeration system includes a compressor, an expansion valve, an evaporator pipe arranged to cool the condensing chamber, and a condenser pipe arranged to dissipate heat away from the condensing chamber; and the apparatus further includes a conduit disposed in sealed fluid communication between the valve assembly and the condensing chamber, a gas flow measurement device, disposed in the conduit, that measures the flow of gas through the conduit, and a control system, coupled to the gas flow measurement device, that determines when a predetermined volume of gas has passed through the conduit.

BRIEF DESCRIPTION OF THE DRAWINGS

Further features, embodiments, and advantages of the present invention will become apparent from the following detailed description with reference to the drawings, wherein.

DETAILED DESCRIPTION OF THE PREFERRED EMBODIMENTS

Figure 1:
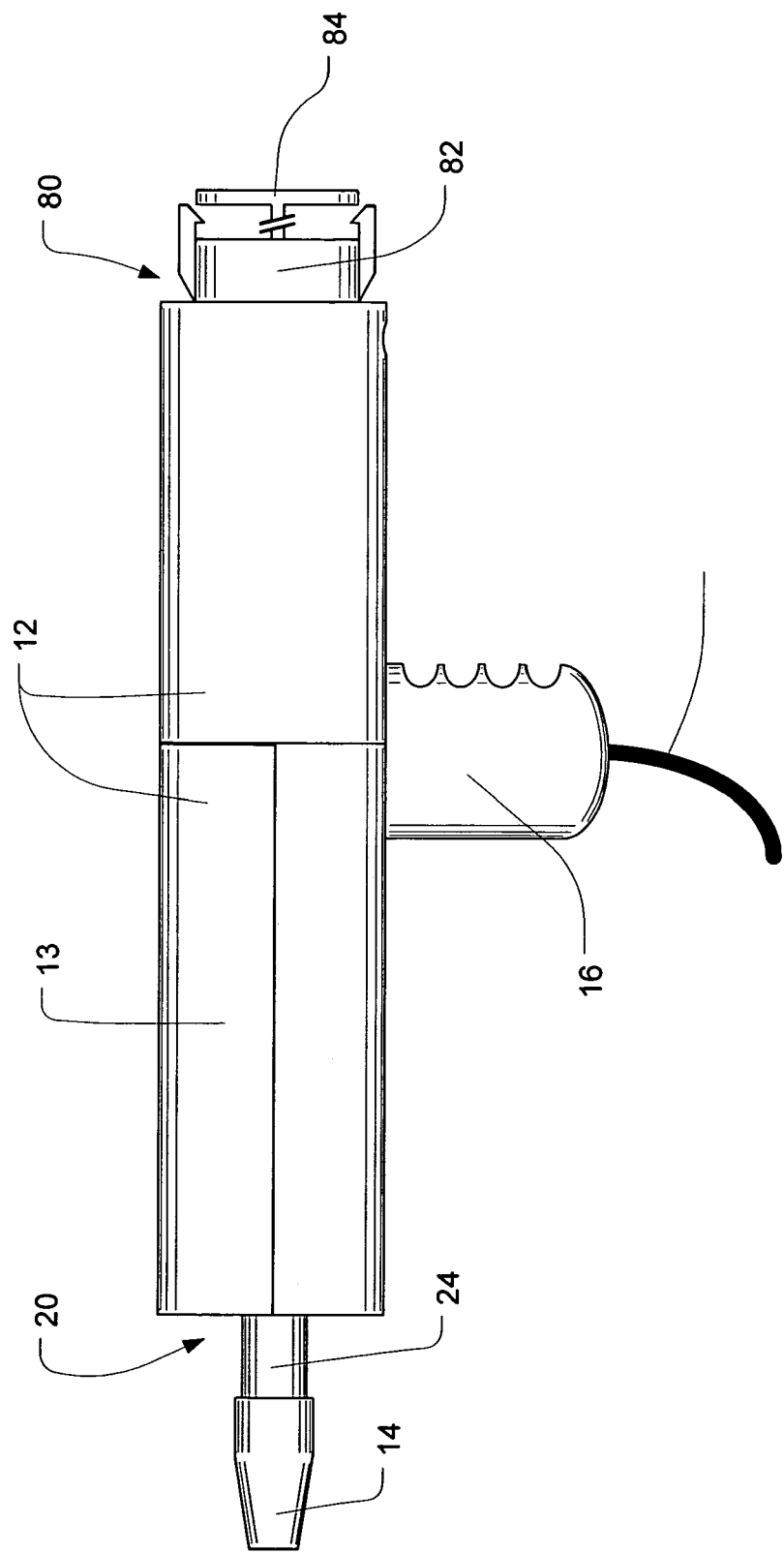
FIG. 1 is a side view of a device for collection of exhaled alveolar breath condensate in accordance with a preferred embodiment of the present invention.

Referring now to the drawings, in which like numerals represent like components throughout the several views, the preferred embodiments of the present invention are next described. The following description of the preferred embodiment(s) is merely exemplary in nature and is in no way intended to limit the invention, its application, or uses.

FIG. 1 is a side view of a device 10 for collection of exhaled alveolar breath condensate in accordance with a preferred embodiment of the present invention. The device 10 includes a housing 12, a disposable mouthpiece 14, a handle 16, an intake cartridge assembly 20 and a syringe 80. The size and shape of the housing 12 and the handle 16 are designed to permit the device 10 to be readily held by a patient, but the device 10 may also be mounted on the side of a hospital bed or gurney, attached to a rolling mobile stand, or the like, using suitable mounting hardware (not shown).

Figure 2:
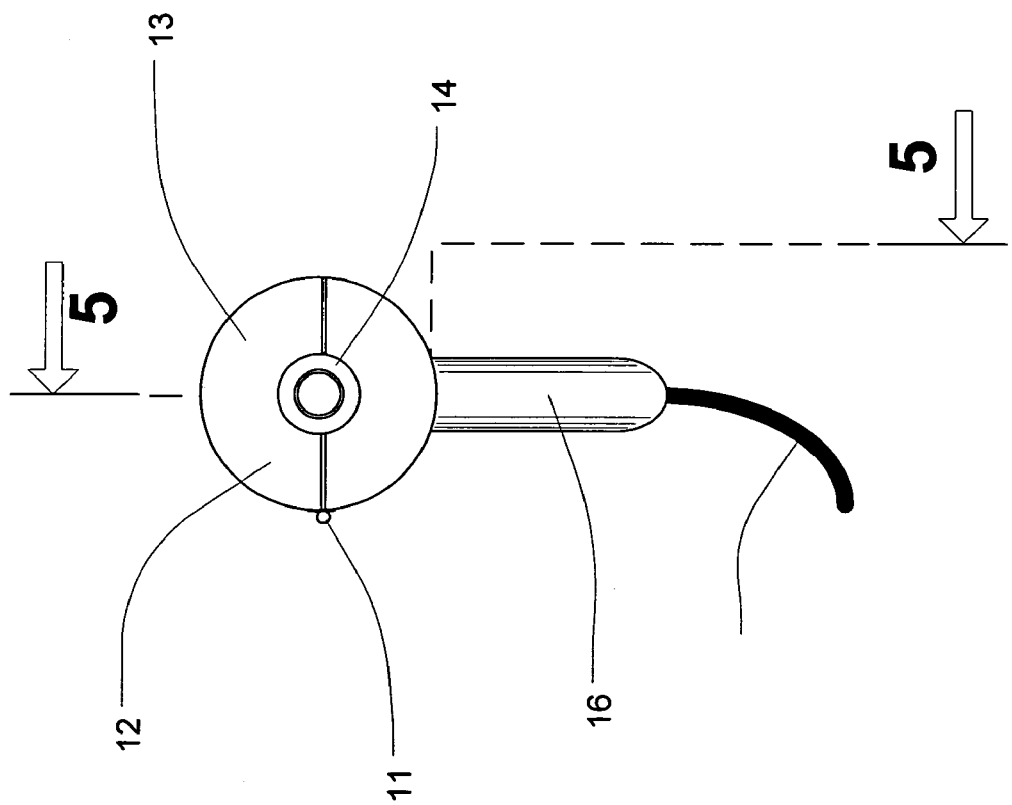
FIG. 2 is a front view of the device of FIG. 1.

FIG. 2 is a front view of the device 10 of FIG. 1. The housing 12 is generally cylindrical and is designed to support the intake cartridge assembly 20 and the syringe 80 therein. The housing 12 includes a cartridge lid 13 secured to the remainder of the housing 12 by a hinge 11. The cartridge lid 13 may thus be opened to facilitate access to the cartridge assembly 20 disposed inside the housing 12.

Figure 3:
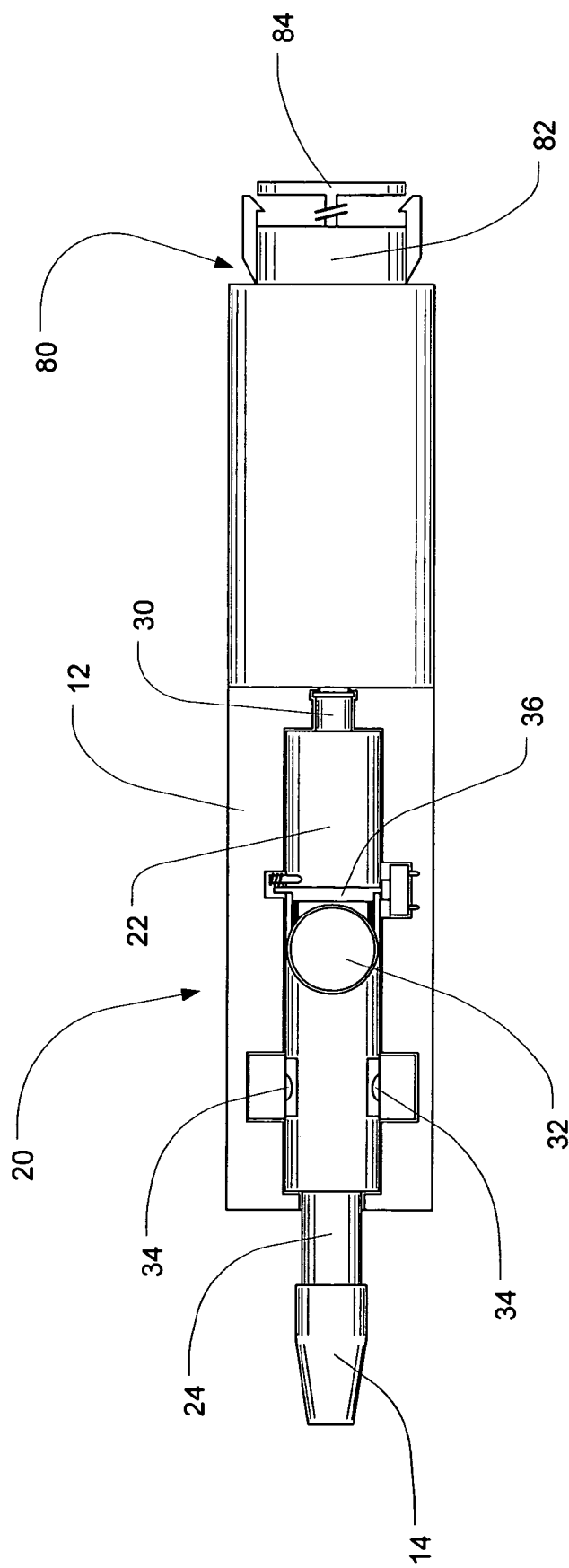
FIG. 3 is a top view of the housing of FIG. 1 with the cartridge lid removed to show the cartridge assembly.
Figure 4:
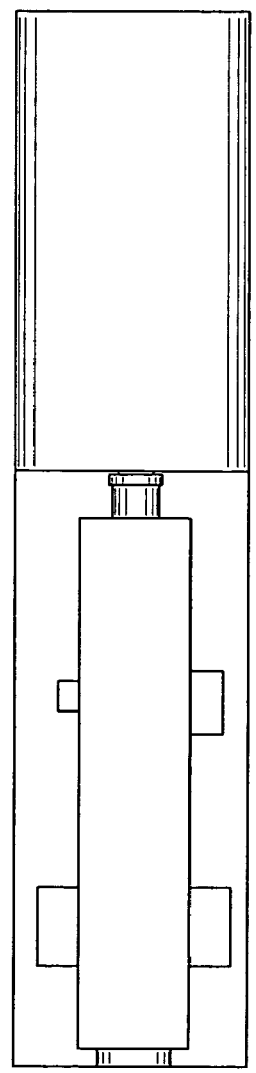
FIG. 4 is a top view of the housing of FIG. 1 with the cartridge assembly and the syringe removed.
Figure 5:
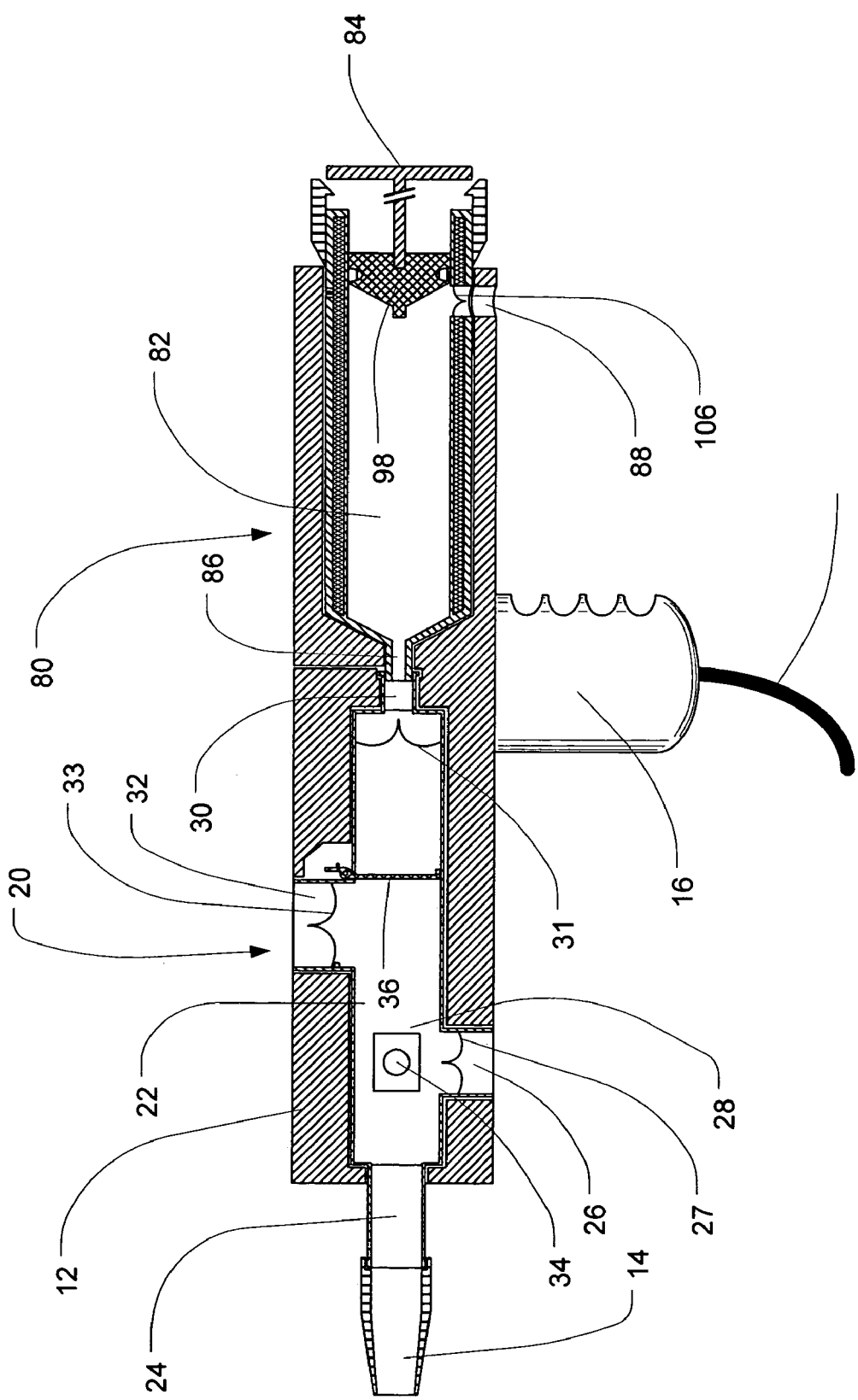
FIG. 5 is a side cross-sectional view of the device of FIG. 2, taken along line 5-5.

FIG. 3 is a top view of the housing 12 of FIG. 1 with the cartridge lid 13 removed to show the cartridge assembly 20, FIG. 4 is a top view of the housing 12 of FIG. 1 with the cartridge assembly 20 and the syringe 80 removed, and FIG. 5 is a side cross-sectional view of the device 10 of FIG. 2, taken along line 5-5. As shown therein, the housing 12 may include a variety of compartments, recesses, pockets or the like for receiving the various components of the device 10. In particular, one end of the housing 12 may be devoted to the components of the cartridge assembly 20, while the other end houses the syringe 80. The housing 10 includes a cartridge compartment, a two spectrometer pockets, an actuator pocket, and other pockets and recesses for various parts and functions described below. In addition, the housing 12 includes external openings through at each end as well as two openings in its bottom and an opening penetrating the cartridge lid 13. The purpose of each of these openings will become apparent hereinbelow.

Figure 6:
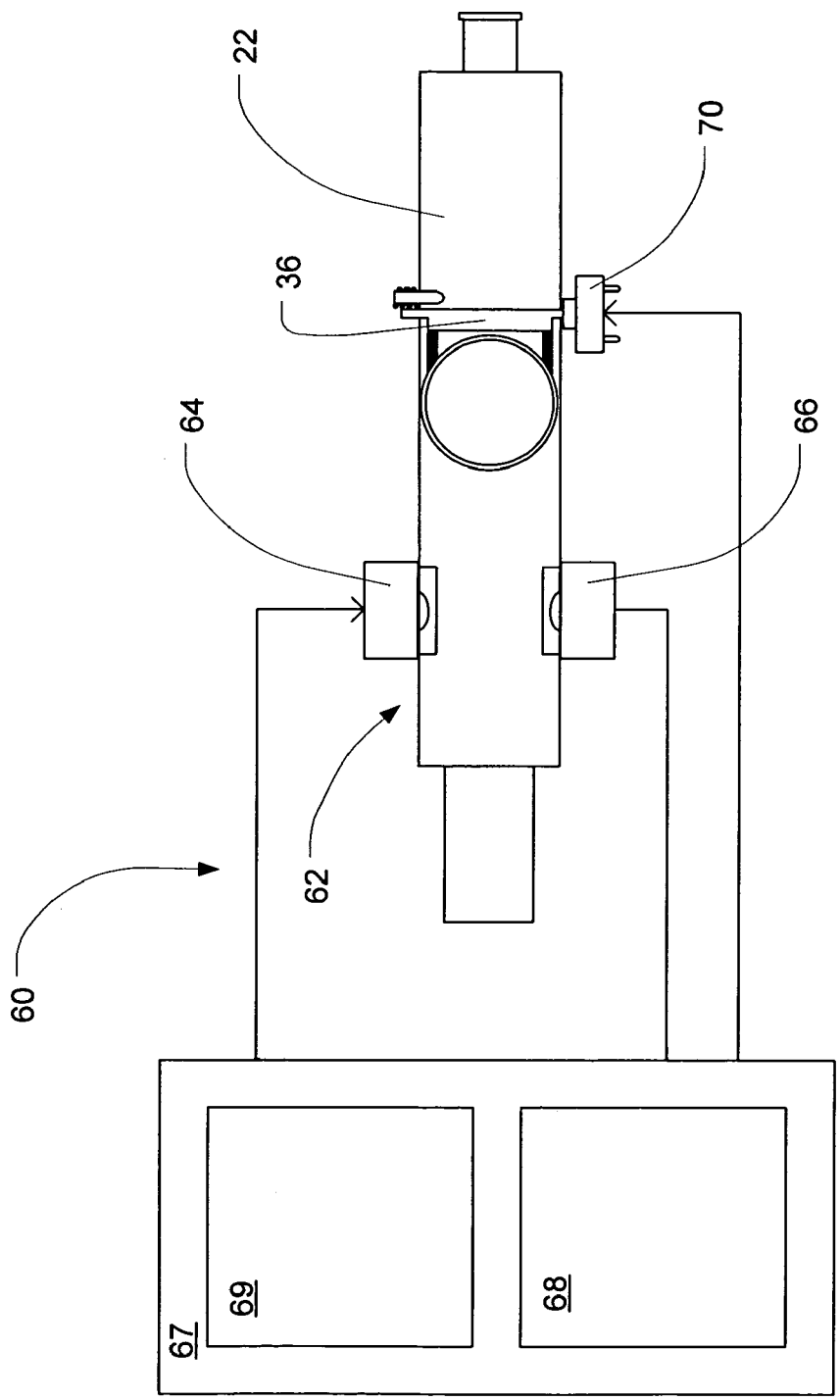
FIG. 6 is a schematic view of the cartridge assembly of FIG. 3.

FIG. 6 is a schematic view of the cartridge assembly 20 of FIG. 3. The cartridge assembly 20 includes a disposable cartridge 22 and a control system 60. The control system 60 is used to control a directional flap 36 in the cartridge 22, which regulates the path of exhaled breath through the cartridge 22. The operation of the control system 60 and the cartridge 22 will be more fully described hereinbelow.

FIGS. 7-10 are perspective, right side, top and rear views of the cartridge 22 of FIGS. 5 and 6. The cartridge 22 may be formed from polyethylene, polycarbonate, polyvinyl, plastic, glass or the like and includes a breathing port 24, an inhalation port 26, an absorption chamber 28, a collection port 30, an exhaust vent 32, a pair of spectrometer windows 34 and a valve assembly that may include the directional flap 36, a spring 50 and a pin or boss 52 protruding from an exterior surface of the cartridge 22. The breathing port 24 is fluidly connected between the absorption chamber 28 and the mouthpiece 14 to permit a user to breathe in and out through the cartridge 22. The inhalation port 26 includes a one-way valve 27 that permits ambient air to be drawn through the cartridge 22 during the user's inhalation cycle. The collection port 30 is in fluid communication with the syringe 80 and includes a one-way valve 31 to prevent gases in the syringe 80 from returning to the cartridge 22. The exhaust vent 32 permits unwanted exhaled breath to be vented to the environment and includes a one-way valve 33 to prevent air from entering the cartridge 22 therethrough. It should be noted that although FIGS. 7 and 10, and some of the other illustrations, show the exhaust vent 32 as being round, it may be preferable for the exhaust vent 32 to be rectangular or some other shape. The emitter and sensor units 64, 66 of a spectrometer or other monitoring system 62 may be stationed adjacent the spectrometer windows 34, as described below, in order to measure the content of gas contained in the absorption chamber 28 of the cartridge 22.

Figure 7:
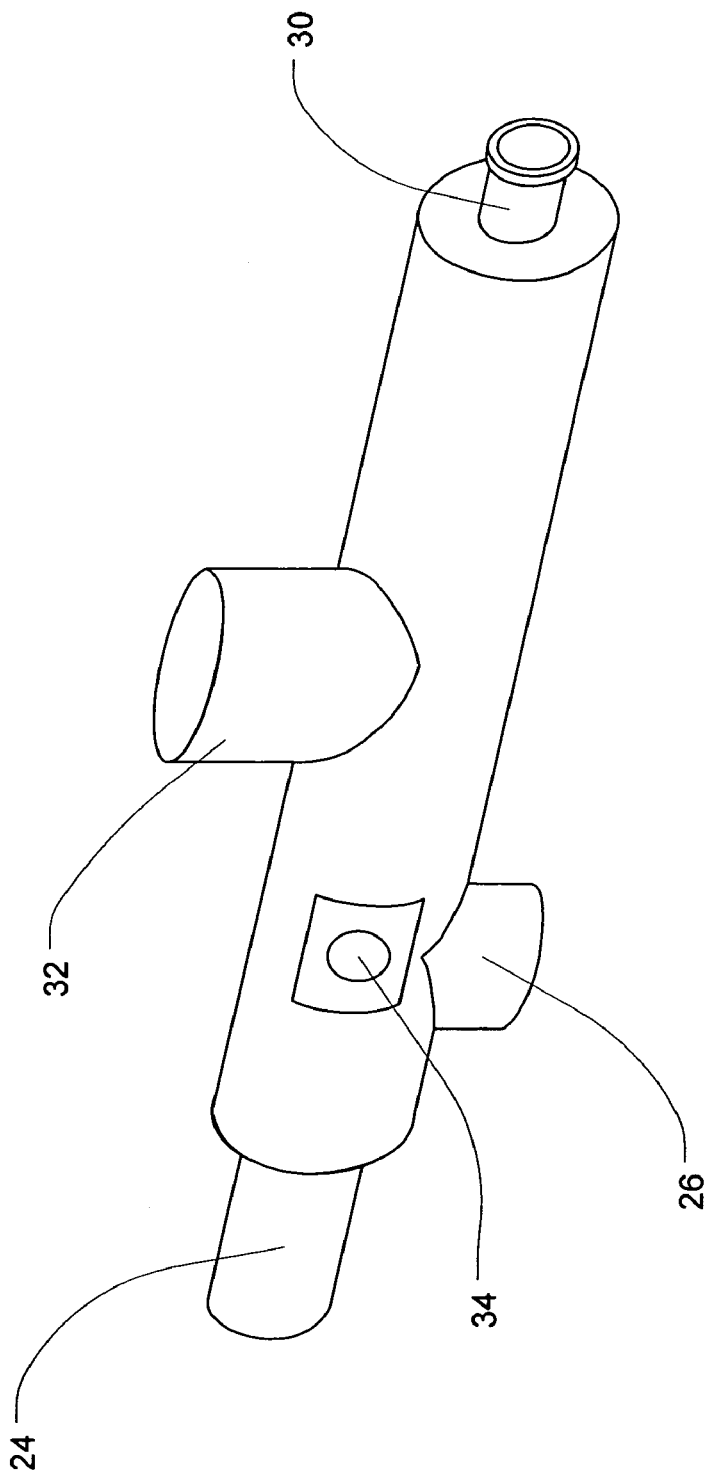
FIG. 7 is an enlarged perspective view of the cartridge of FIG. 1.
Figure 8:
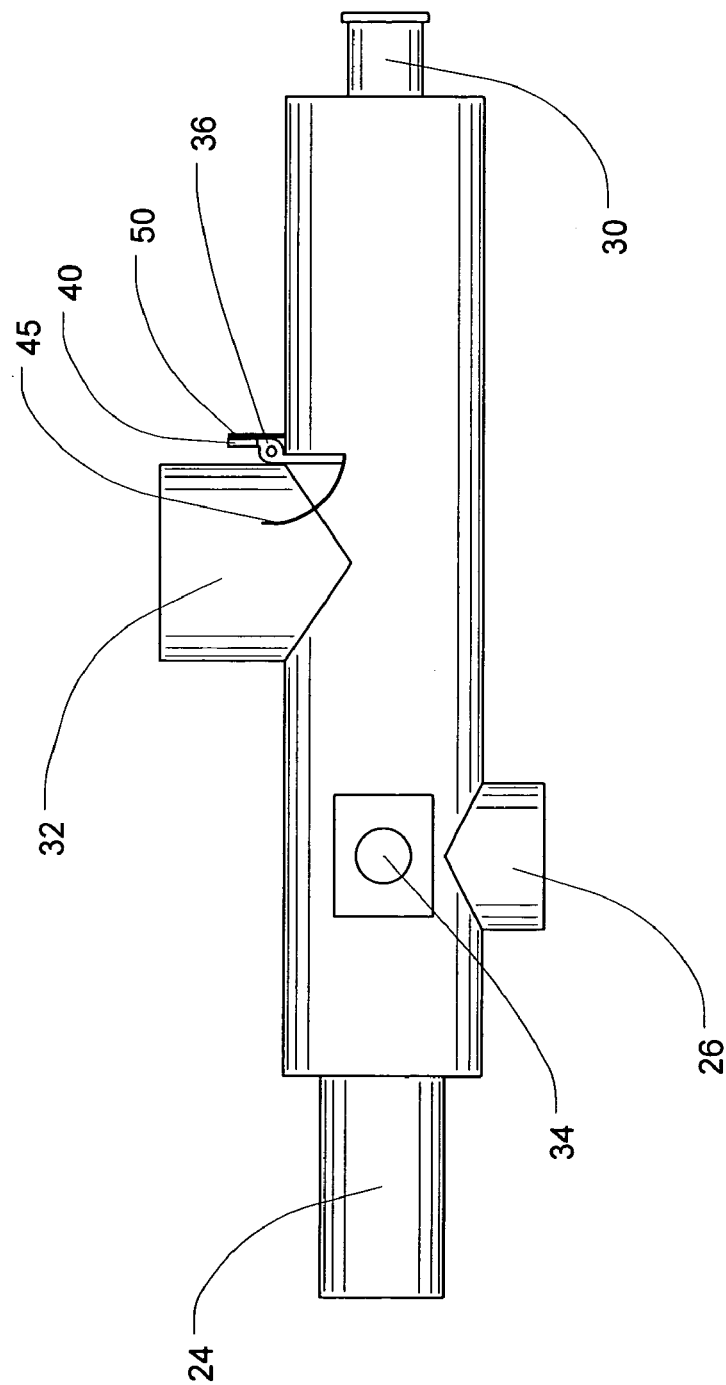
FIG. 8 is a right side view of the cartridge of FIG. 7.
Figure 9:
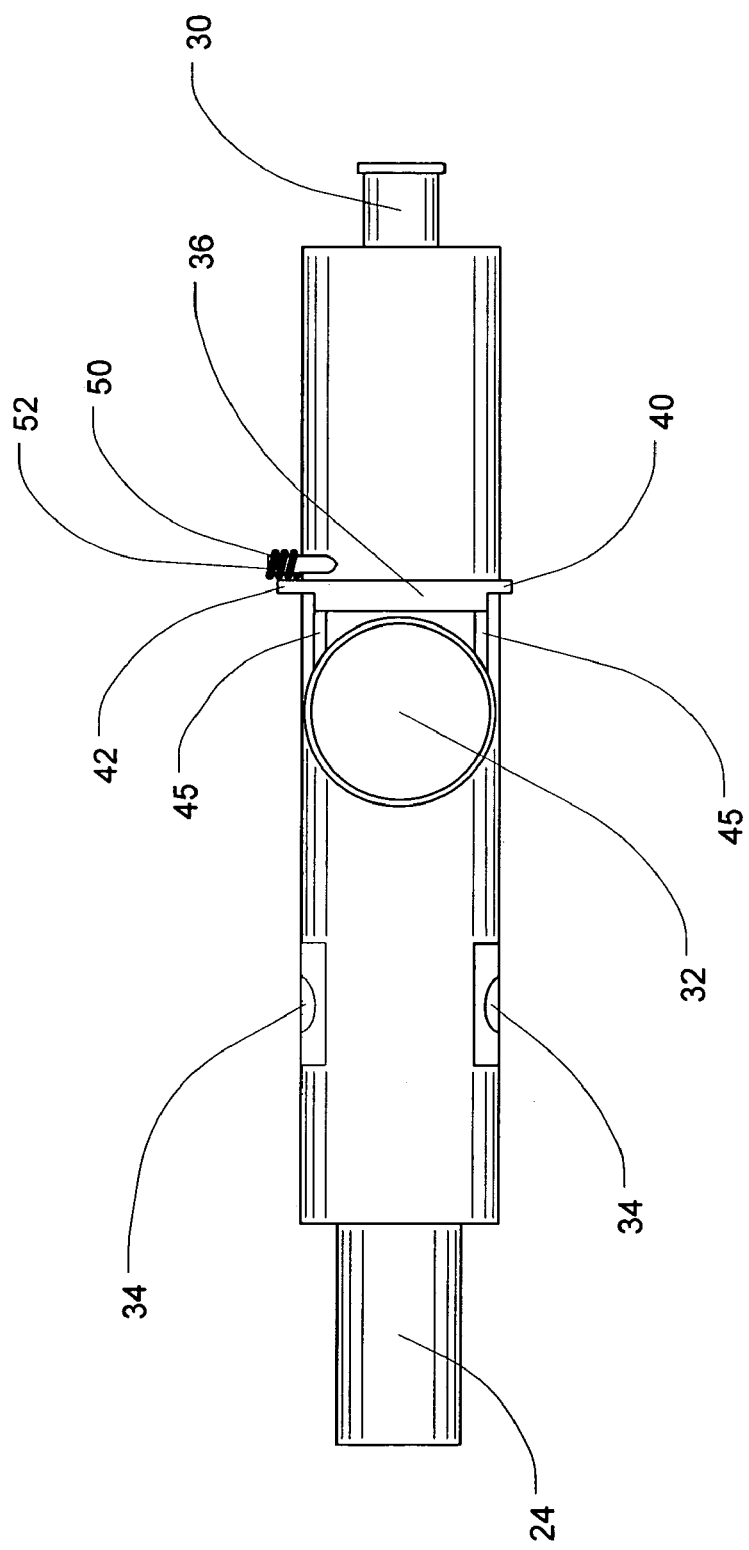
FIG. 9 is a top view of the cartridge of FIG. 7.
Figure 12:
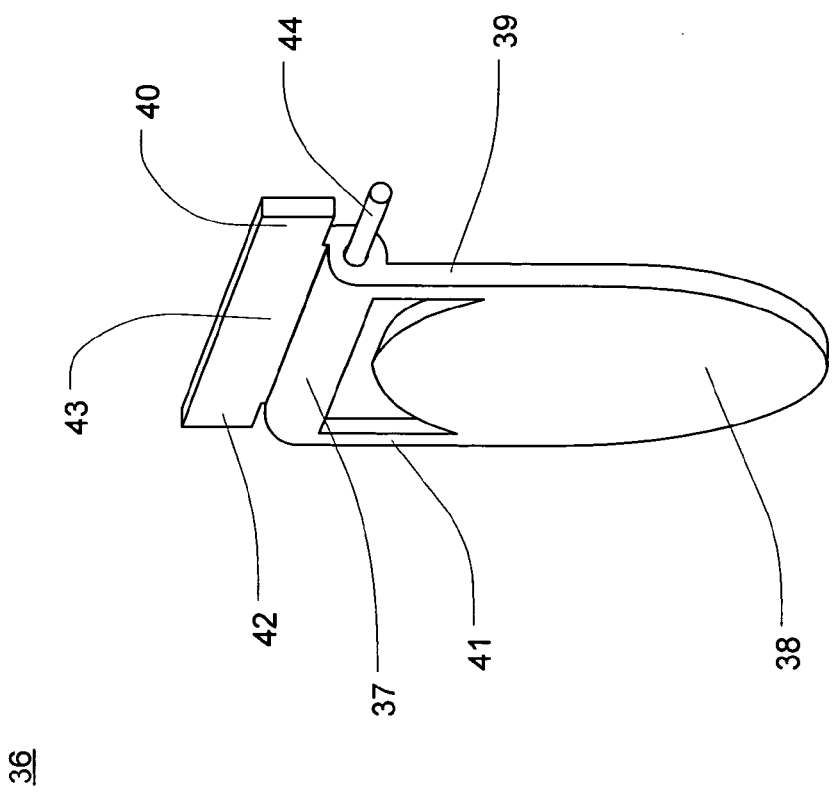
FIG. 12 is a side perspective view of the directional flap of FIG. 7.
Figure 11:
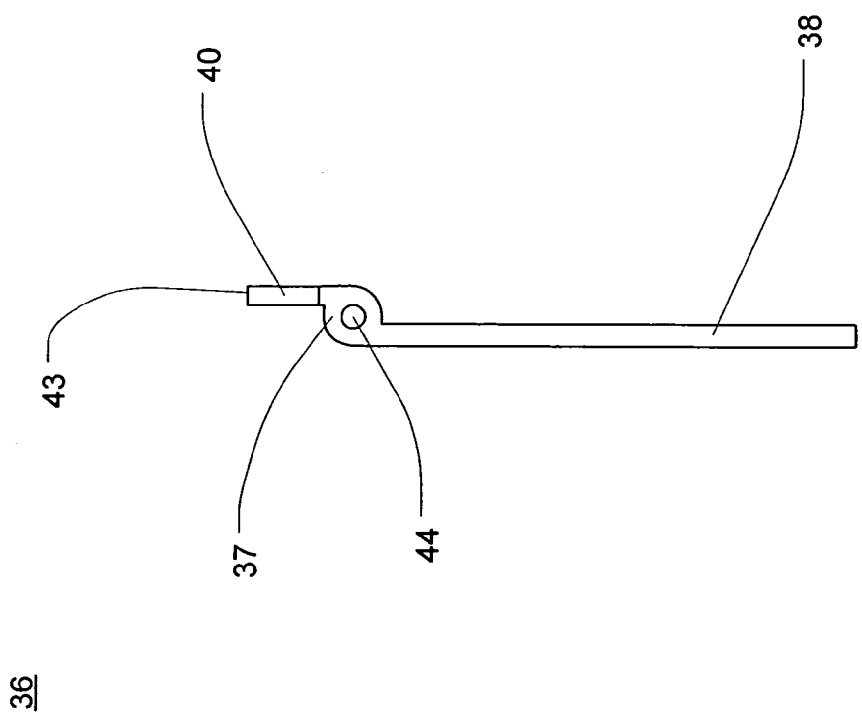
FIG. 11 is a side view of the directional flap of FIG. 7.

FIGS. 11 & 12 are side and perspective views, respectively, of the directional flap 36 of FIG. 7. The directional flap 36 includes a central shaft 37, arranged around an axial pin 44, from which a deflector plate 38 is supported by a pair of arms 39, 41. As illustrated in FIG. 8, a pair of tabs 40, 42 extend laterally from the ends of a flange 43, supported by the central shaft 37, for purposes made clear hereinbelow. The directional flap 36 may be adjusted to force the exhaled breath in the interior of the cartridge 22 to be exhausted either through the collection port 30 or the exhaust vent 32. As perhaps best shown in FIGS. 8 and 9, the flap 36 is supported in the interior if the cartridge 22 by the arms 39, 41, which extend through slots 45 in the sides of the cartridge 22.

Figure 10:
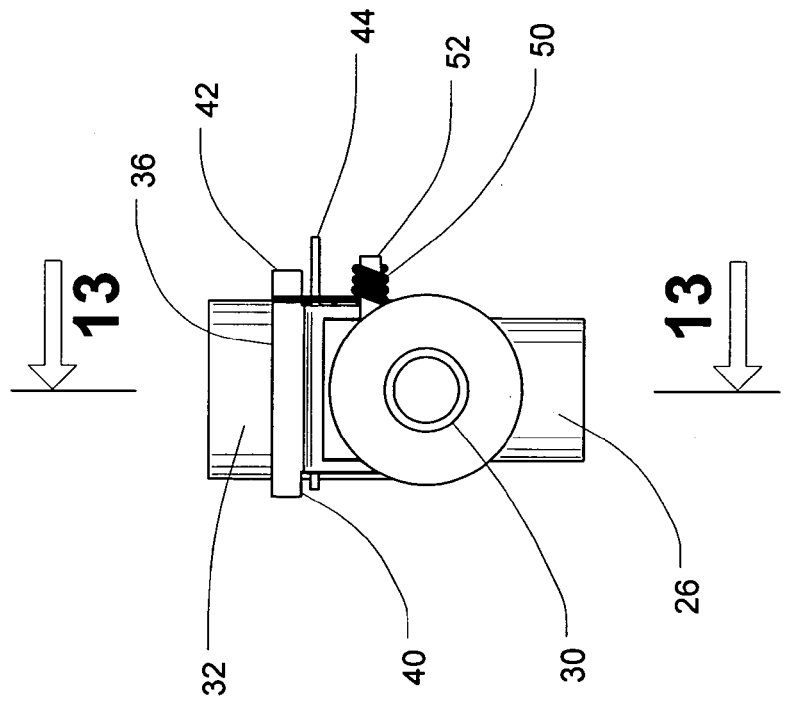
FIG. 10 is a rear view of the cartridge of FIG. 7.
Figure 13:
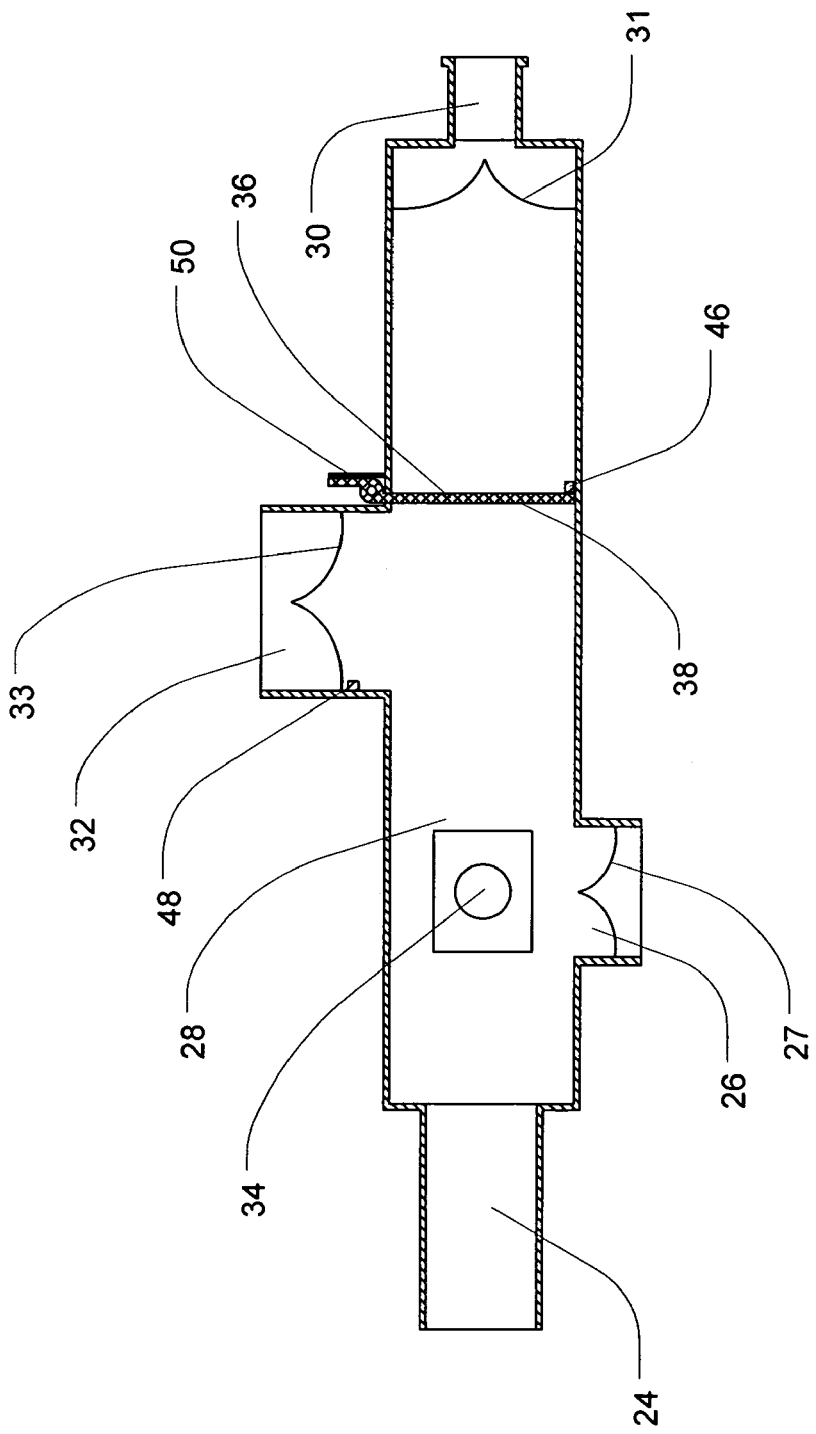
FIG. 13 is a partially-schematic side cross-sectional view of the cartridge of FIG. 10, taken along line 13-13, showing the directional flap in a closed position.
Figure 14:
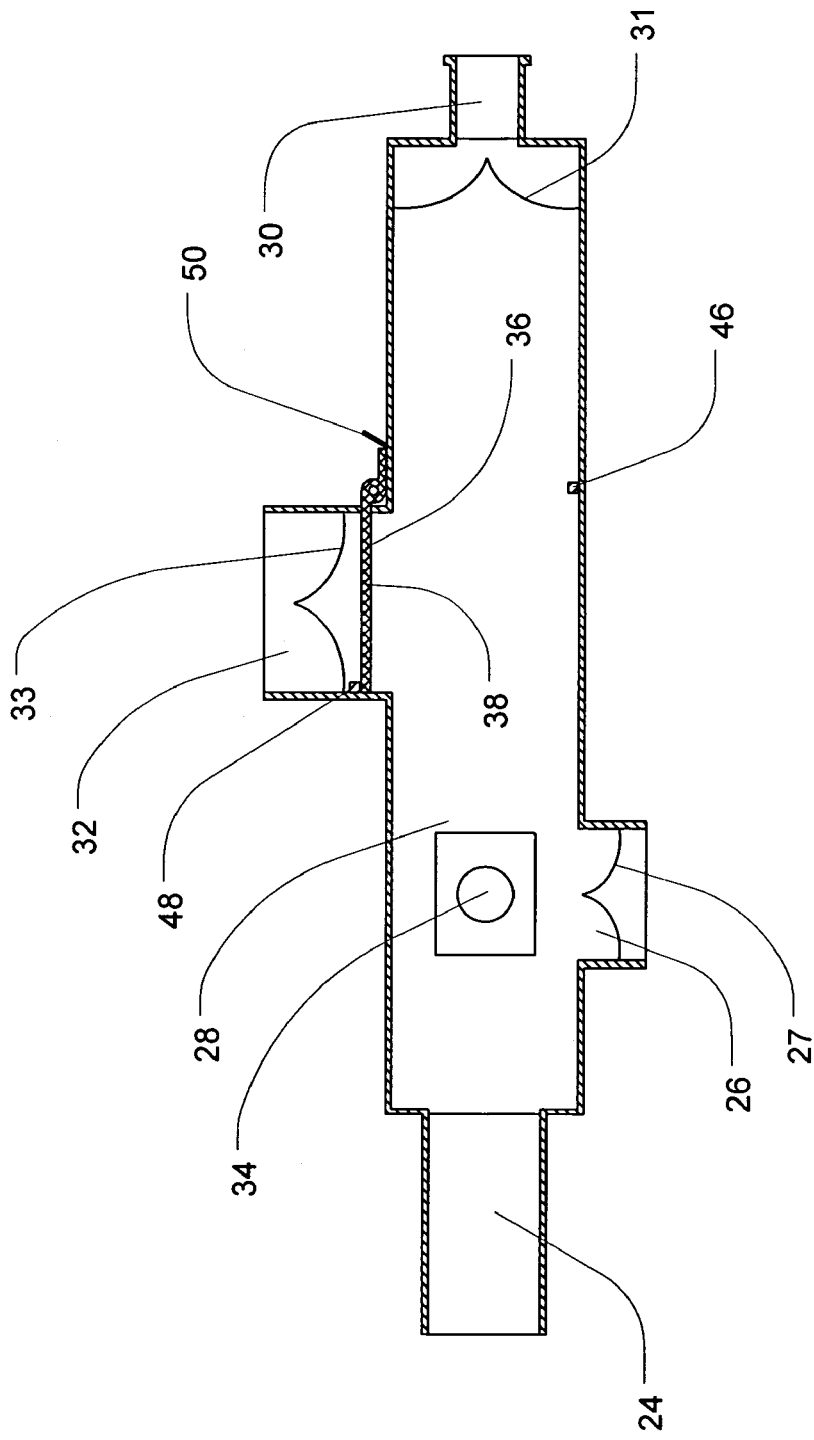
FIG. 14 is a partially-schematic side cross-sectional view of the cartridge of FIG. 10, taken along line 13-13, showing the directional flap in an open position.

FIGS. 13 and 14 are partially-schematic side cross-sectional views of the cartridge 22 of FIG. 10, taken along line 13-13, showing the directional flap 36 in a closed position and an open position, respectively. In the closed position shown in FIG. 13, the deflector plate 38 blocks the air path to the collection port 30 that forms the portal between the cartridge 22 and the syringe 80. This forces all expelled breath to be exhausted through the exhaust vent 32. On the other hand, in the open position shown in FIG. 14, the deflector plate 38 covers the exhaust vent 32, forcing all expelled breath through the collection port 30 and into the syringe 80. Preferably, gaskets 46, 48 or other sealing devices and methods may be used to seal the deflector plate 38 and any other necessary surfaces of the directional flap 36 to the various internal structures of the cartridge 22 in order to ensure that gases of the wrong type are not passed through the wrong opening.

Figure 15:
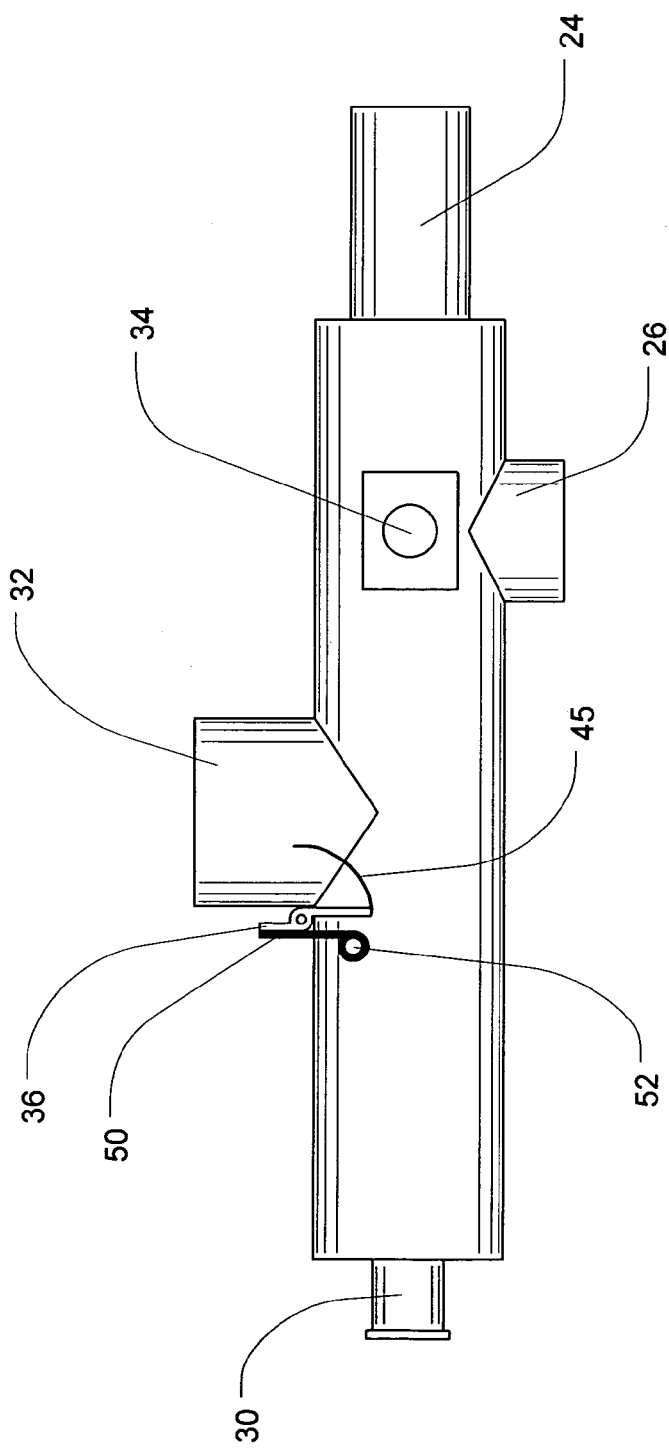
FIG. 15 is a left side view of the cartridge of FIG. 7 showing the attachment of a spring to the directional flap.

FIG. 15 is a left side view of the cartridge 22 of FIG. 7 showing the attachment of the spring 50 to the directional flap 36. The spring 50 or an equivalent device is preferably provided in order to bias the directional flap 36 in a normally-closed position. One purpose of this is to prevent gases and fluids collected in the syringe 80 from escaping back through the cartridge 22. In one embodiment, the spring 50 is a simple coil spring that is interconnected between one of the tabs 42 on the directional flap 36 and the boss 52 on the exterior surface of the cartridge 22, as perhaps best shown in FIGS. 9 and 10. Other biasing devices and methods will be apparent to one of ordinary skill in the art.

Moreover, it will be apparent that the valve assembly may take on any number of different constructions. For example, the directional flap 36 and the biasing device may be internalized within the cartridge 22 in order to provide better sealing, improve operation, or the like. Further, the valve assembly may include two flap-type valves operating in conjunction with each other instead of the single flap 36 disclosed and described herein, or the directional flap 36 may be replaced with a valve mechanism of any suitable alternative type, including but not limited to one rotary valve, a sliding door, a slip barrel, a plunger, or the like, with corresponding changes to the cartridge, biasing device, and the like being apparent to those of skill in the art.

Figure 16:
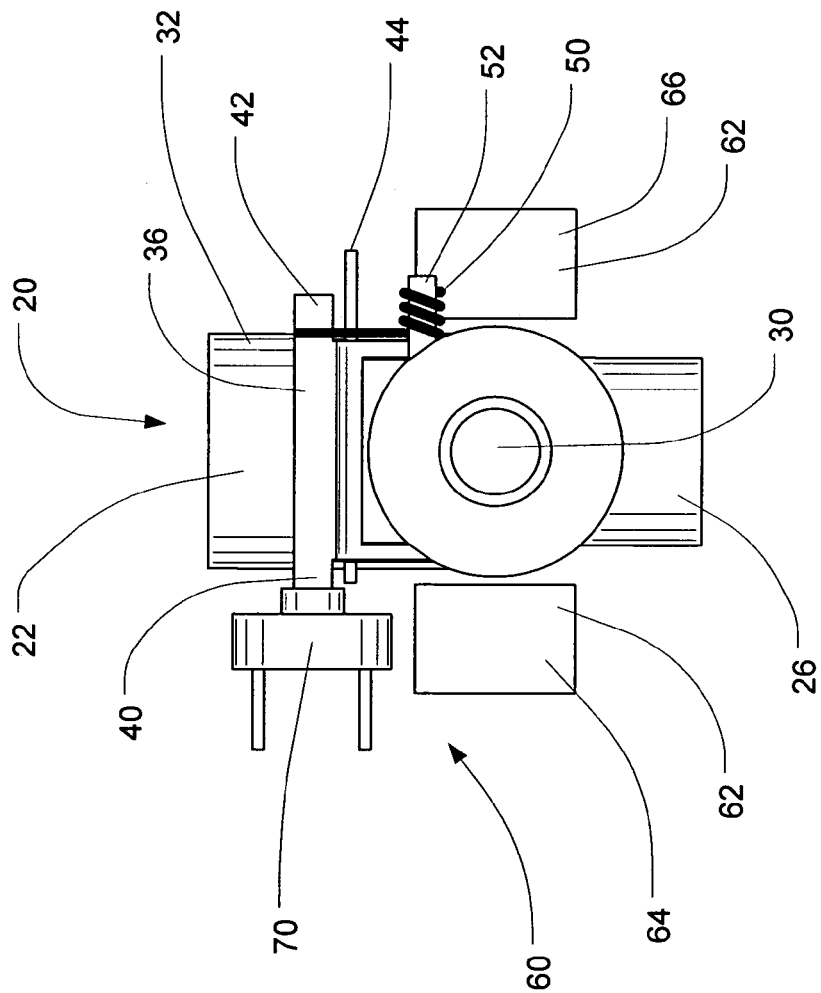
FIG. 16 is a rear view of the cartridge assembly of FIG. 3, shown removed from the housing.

Returning to FIG. 6, the control system 60 includes a monitoring system 62, a control unit 67 and an actuator device 70. The control unit 67 may include an amplifier/differentiator 68 and a monitoring system controller 69. A variety of monitoring systems may be employed using different physical phenomena as triggers for the directional flap. One monitoring system 62 suitable for use in the preferred embodiments of the present invention is a spectrometer, which may be of any conventional type, including infrared (IR), laser, and the like, and includes a radiation source, or emitter unit 64, disposed on one side of the absorption chamber 28 and a sensor unit 66 disposed on the opposite side, adjacent the spectrometer windows 34. FIG. 16 is a rear view of the cartridge assembly 20 of FIG. 3, shown removed from the housing 12. In operation, radiation from the emitter unit 64 passes through the spectrometer window on one side of the cartridge 22, through the absorption chamber 28 and through the absorption window 34 to the sensor unit 66, where the received radiation is analyzed.

IR spectrometers may use chopped IR light emission, where the emission is chopped at a frequency appropriate to distinguish absorbance of the gas of interest, such as $CO_2$, from background absorbance. Alternatively, laser diode spectrometry can be used for detection of more than one gas for the purpose of actuating the directional flap and for the purpose of determining the presence of various pathophysiological processes that are specific to certain disease states. Lasers using AlGaAs, AlGaInP or a Vertical Cavity diodes operating in the near infrared or visible light spectrum at room temperature and ambient pressure in the 1-100 mW power range will be sufficient. The physical length between the emission and detection probe will be approximately 1-3 cm, but the apparent pathlength may be increased by light reflection using dielectrim mirrors to increase sensitivity. Detection wavelengths will be 1390 nm for $CO_2$ and 760 nm for $O_2$, but other gases may be detected by the laser to assist in diagnosis of specific diseases, including lung ischemia, by the detection of the relative amounts of nitric oxide (NO) at 1800 nm and carbon monoxide (CO) at 1570 nm. It is anticipated that further research will reveal significance of laser-based quantification of other inorganic gases and volatile organic compounds to serve as adjuncts to the chemical analyses of the breath condensate in arriving at a final diagnosis of certain disease processes.

Spectrometers are available from a variety of manufacturers, and the selection and implementation of one suitable for use with the present invention would be apparent to one of ordinary skill in the art. As is well known, the sensor unit 66 measures the percent transmission of the radiation to allow measurement of the partial pressure of certain gases in the absorption chamber 28. Measured gases may include carbon dioxide, oxygen, nitrogen, nitrogen oxides, carbon monoxide, aliphatic and aromatic hydrocarbons, isoprostenoid derivatives, or amino acids dissolved in exhaled aerosolized droplets.

Figure 17:
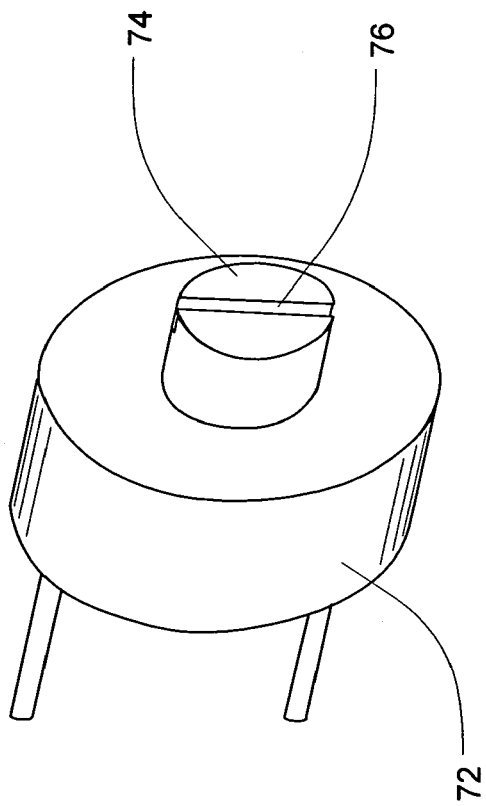
FIG. 17 is an enlarged perspective view of the rotary solenoid of FIG. 16.

One type of actuator device 70 suitable for use in the preferred embodiments of the present invention is a rotary solenoid. The rotary solenoid 70 utilizes a clutch mechanism to adjust or move the directional flap 36 back and forth between its open and closed positions. FIG. 17 is an enlarged perspective view of the rotary solenoid 70 of FIG. 16. As illustrated therein, an actuator shaft 74 extends from the solenoid body 72. A slot 76 in the end of the actuator shaft 74 may be firmly coupled to one of the tabs 40 on the directional flap 36 in order to provide rotational movement to the tab 40 and likewise rotating the directional flap 36 between its open and closed positions. If necessary, the directional flap tab 40 and the actuator shaft 74 of the rotary solenoid 70 may be disposed coaxially with the pin 44 of the directional flap in order to minimize wear on the components. Rotary solenoids 70 are available from a variety of manufacturers, and the selection and implementation of one suitable for use with the present invention would be apparent to one of ordinary skill in the art. It should also be apparent that other actuating devices and methods may be employed without departing from the scope of the present invention, including pulley mechanisms, magnetic actuation of a metallic valve, and the like, triggered from expired volume measured from a flow transducer rather than from light-absorption technique.

Figure 18:
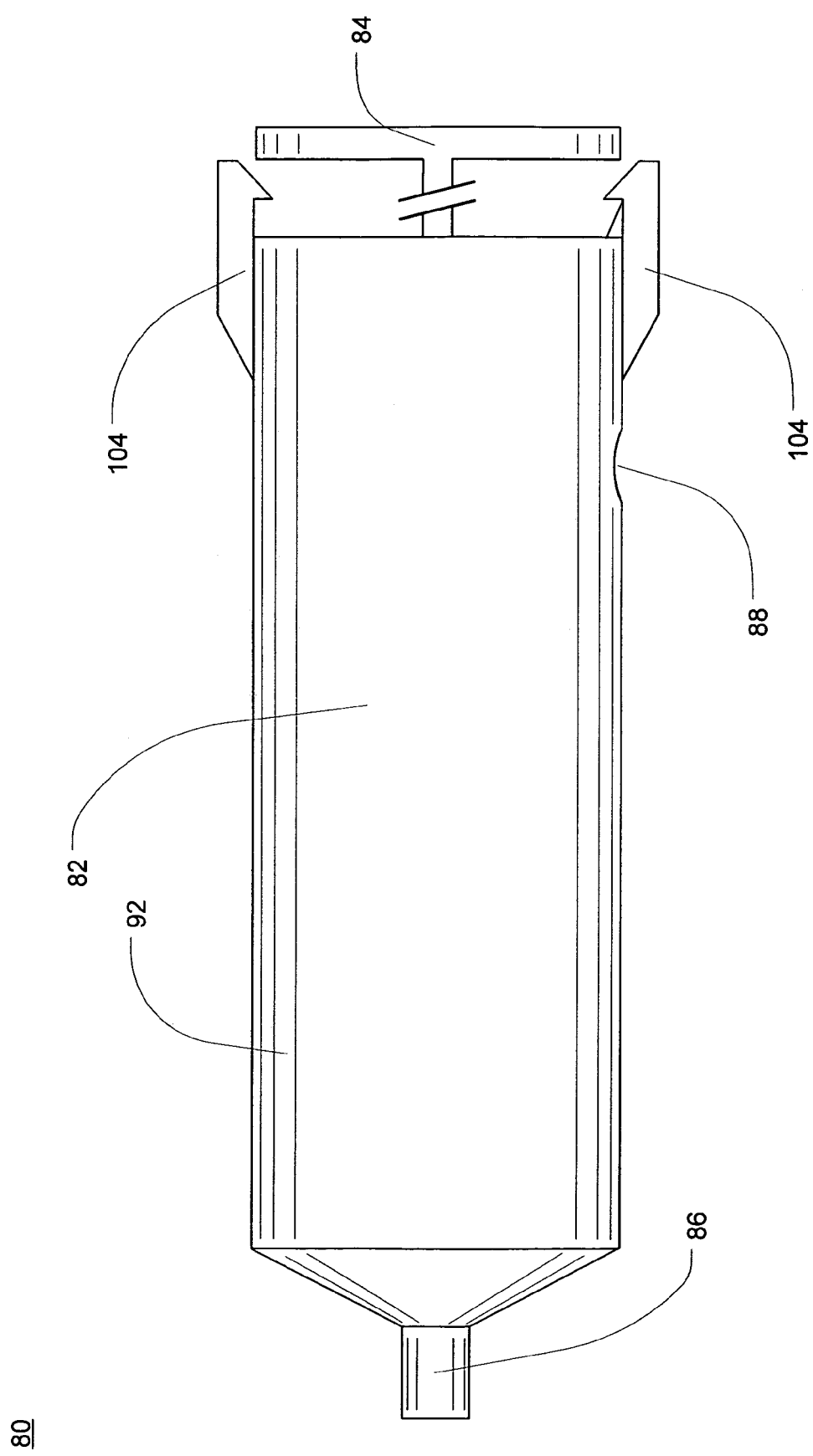
FIG. 18 is a side view of a first exemplary syringe for use in the device of FIG. 1.
Figure 19:
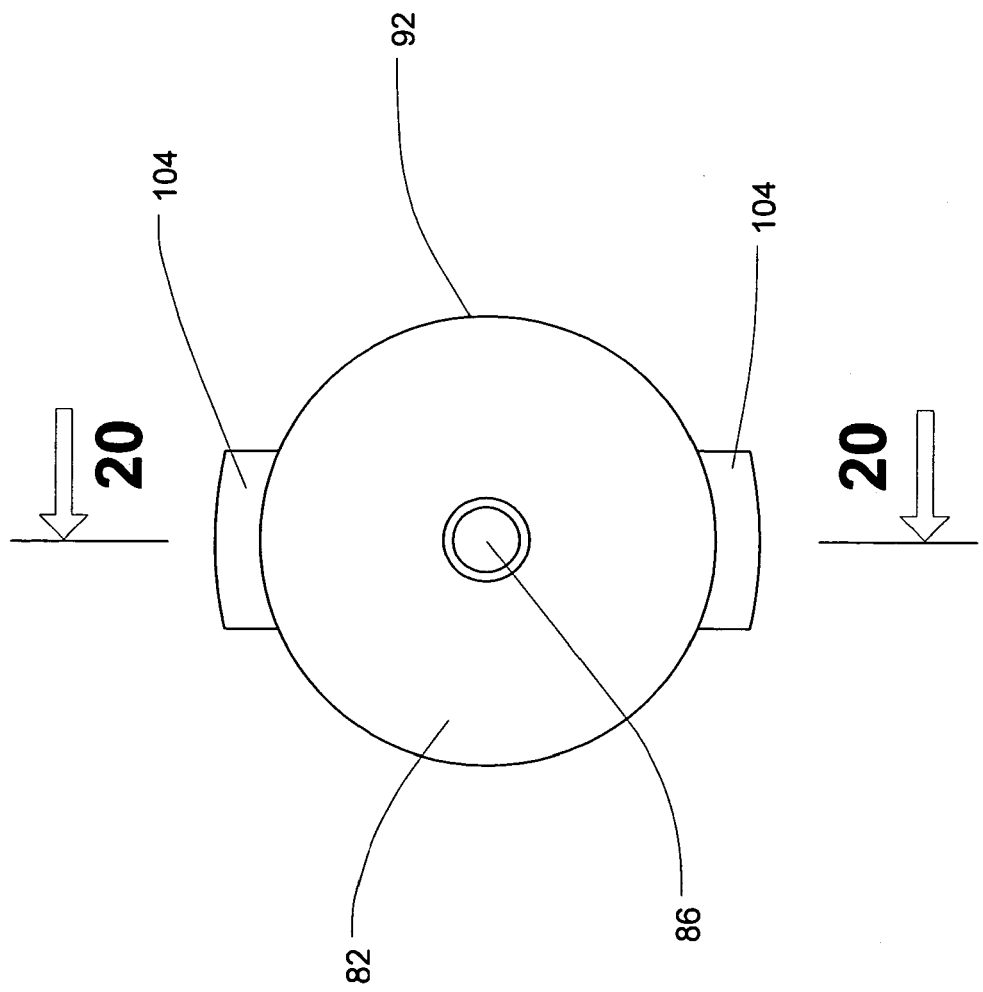
FIG. 19 is a front view of the syringe of FIG. 18.

FIGS. 18 and 19 are side and front views, respectively, of a first exemplary syringe 80 for use in the device 80 of FIG. 1. As illustrated therein, the syringe 80 includes an insulated condensing chamber 82 having a plunger assembly 84, an inlet 86 and an exhaust port 88. The condensing chamber 82 may be constructed of any suitable material, including, but not limited to, glass, plastic, polyethylene, polycarbonate, or polyvinyl or other synthetic polymer.

Figure 20:
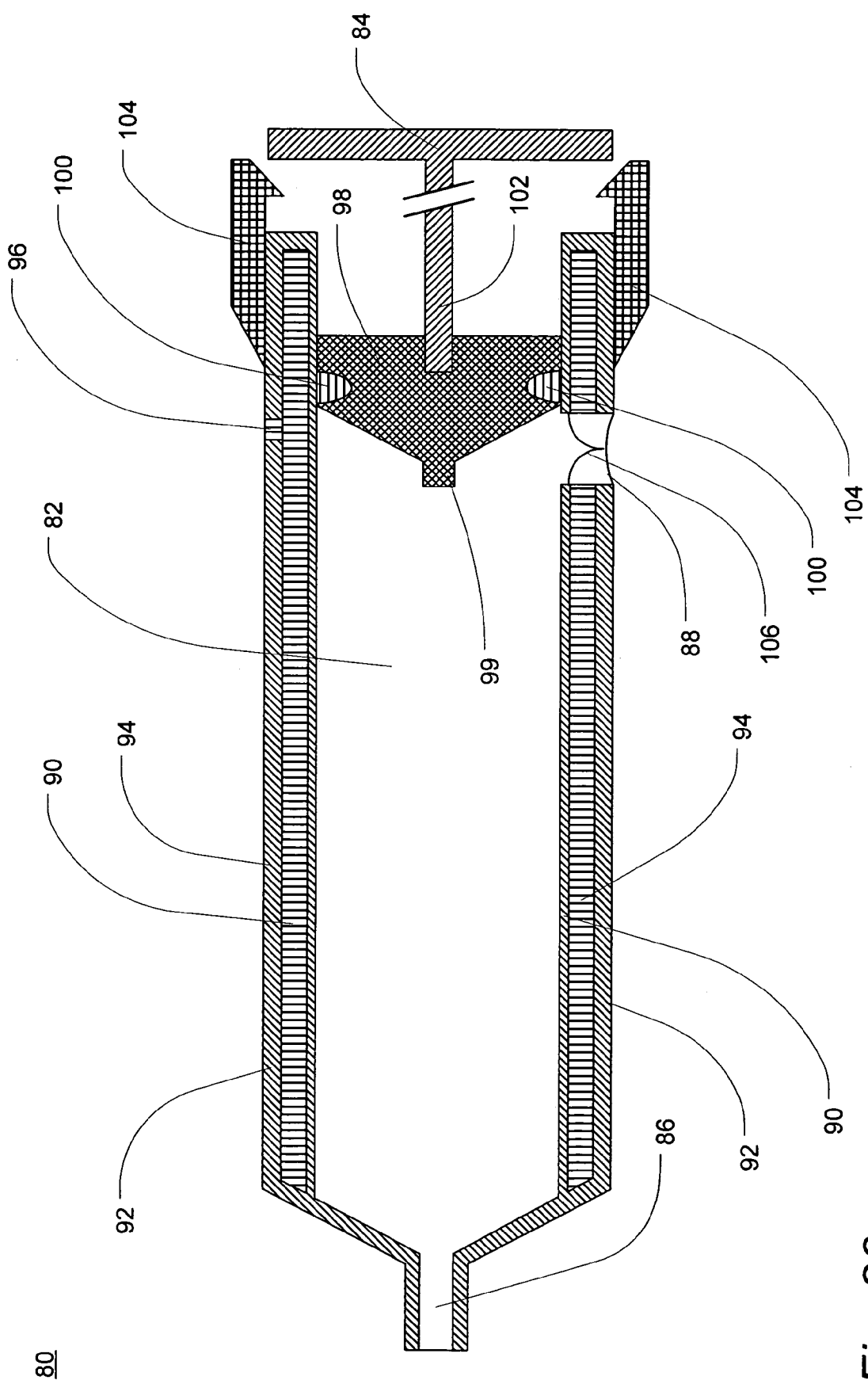
FIG. 20 is a side cross-sectional view of the syringe of FIG. 19, taken along line 20-20.

FIG. 20 is a side cross-sectional view of the syringe 80 of FIG. 18, taken along line 20-20. As shown therein, the insulative effect of the condensing chamber 82 may be provided by any of a variety of materials either formed directly into the walls (not illustrated) of the condensing chamber or sandwiched between an inner wall 90 and an outer wall 92. Arranged peripherally between the inner and outer walls 90, 92 is a layer of a material 94 suitable for creating an endothermic reaction, such as $NH_4NO_3$, that has been vacuum-packed and sealed. The condensing chamber 82 is preferably provided with a needle port 96 or some other means for permitting the sealed material 94 to be hydrated or otherwise injected with a readily available catalyst in order to trigger an endothermic reaction when the syringe 80 is ready to be used. If $NH_4NO_3$ is to be used, then the $NH_4NO_3$ may be hydrated with water in a 1:4 molar ratio. Such a material is preferred because a user may trigger the reaction by injecting the $NH_4NO_3$ material with a preset volume of tap water or saline via the needle port 96, similar to the way a nurse would "flush" an IV line. However, other materials may likewise be used to create a suitable endothermic reaction.

The inner surfaces of the condensing chamber 82 define a central cylinder in which is fitted the plunger assembly 84. The plunger assembly 84 includes a piston 98, a rubber gasket 100, a handle 102 extending from one end of the condensing chamber 82, and a clip assembly 104 disposed at the handle end of the condensing chamber 82. The inlet 86 is preferably disposed at the opposite end of the condensing chamber 82 from the plunger assembly 84 and may be arranged in the form of a nipple. The exhaust port 88 is preferably disposed at the same end of the condensing chamber 82 as the handle 102 and is equipped with a one-way valve 106 to permit gases passing through the condensing chamber 82 to be exhausted therethrough while preventing ambient gases from entering the condensing chamber 82.

Although not shown herein, a second exemplary syringe suitable for use (with minor modifications) in the device 10 of FIG. 1 is a double-walled syringe of a type somewhat similar to one disclosed in the commonly-assigned U.S. Provisional Patent Application No. 60/434,916, filed Dec. 20, 2002. The construction of this syringe is similar to that of the first, except that the space between the inner and outer walls of the condensing chamber is filled with water, polyethylene glycol ("PEG"), or another suitable coolant material and the outer wall is then sealed to the inner wall to prevent leakage. A syringe of this type may be cooled by placing it in a standard freezer prior to use in order to lower the temperature of the syringe to less than 0° F., and preferably to less than 0° C. Details of this type of syringe are provided in the aforementioned provisional patent application.

In operation, the housing lid 13 is opened and the cartridge assembly 20 is inserted into the housing 12 such that the various components are snapped into place in their respective compartments in the housing 12. Next, a syringe 80 of one of the types described above is retrieved from storage and inserted into the open end of the housing 12, nipple-shaped inlet 86 first, and pushed inward until the inlet 86 is coupled to the collection port 30 of the cartridge 22.

Depending on the syringe type, the syringe 80 may have been stored in a refrigeration device, such as a conventional household freezer, that is capable of lowering the temperature to less than 0° F., and preferably less than 0° C., in order to freeze the jacket of coolant material 94 contained between the inner and outer walls 90, 92 of the condensing chamber 82. Alternatively, syringes of the endothermic reaction type may merely be stored at an ambient temperature and then cooled to the desired temperature by triggering an endothermic reaction therein when ready for use. If the mouthpiece 14 is stored separately from the rest of the device 10, then the mouthpiece 14 may be assembled to the cartridge assembly 20. In some applications, such as when the device 10 is to be attached to a bed or to a rolling stand, it may be useful to connect the mouthpiece 14 to a longer tube (not shown) in sealed fluid communication with the breathing port 24 of the cartridge 22.

Once the device 10 is assembled, the patient positions the mouthpiece 14 in sealed relationship to his mouth area and inhales and exhales through the mouthpiece 14. When the patient inhales, ambient air enters through the inhalation port 26 via the one-way valve 27. The exhaled breath is guided into the absorption chamber 28 via the breathing port 24. Under the control of the monitoring system controller 69, the spectrometer 62 measures the partial pressure of certain gases in the absorption chamber 28 and delivers an analog current to the amplifier/differentiator 68. For example, the magnitude of the analog signal may be proportional to the amount of $CO_2$ present in the absorption chamber 28.

At the beginning of an expiration by the patient, the patient's breath is dilute in carbon dioxide and rich in oxygen. In one preferred embodiment, the rotary solenoid 70 and the amplifier/differentiator 68 are calibrated such that the directional flap 36 remains in its resting state, wherein the flap 36 is held in its closed position by the spring 50, and the airway deadspace is shunted out the exhaust vent 32 to the environment. As the patient's alveoli begin to empty during expiration, the partial pressure of $CO_2$ increases and the partial pressure of oxygen decreases. The resulting signal generated by the amplifier/differentiator 68 eventually activates the solenoid 70, causing the directional flap 36 to open. At this point, the alveolar gas and associated water content are directed selectively to the syringe 80.

To maximize the efficiency of collection of breath condensate, the deadspace volume of the cartridge 22 should preferably be minimized to less than 20 mL. It will also be preferable for patients to exhale deeply through the device 10 in order to enhance the amount of condensation in the alveolar phase. Thermodynamic and kinetic modeling has suggested that forced exhalation will enhance the transfer of alveolar water into vapor and droplet phase. Thus the device 10 is preferably designed to impart a small resistance to exhaled flow. The outlet diameter and length of the collection port 30, connected to the condensing chamber 82, will be calibrated to provide a small amount of resistance to exhalation, which the patient should be able to detect, but which is not enough to cause exhalation to be excessively laborious.

As portions of the expired breath pass into the syringe 80, the moisture in the breath begins to condense on the inner surfaces of the condensing chamber 82. Because of the depressed temperature of the condensing chamber 82, condensate begins to collect and may immediately freeze on the inner surfaces thereof. Once the patient's breath has warmed the condensing chamber 82 sufficiently, the condensate will melt and may be expressed from the condensing chamber 82. The construction of the condensing chamber 82 is preferably calibrated to provide a sufficient quantity of condensate (approximately 250 microliters) after a predetermined number of breaths. When sufficient condensate has been collected, the syringe 80 may be removed from the housing 12 and the plunger assembly 84 depressed to force the collected condensate from the nipple 86 as described previously. Finally, once the condensate has been collected and withdrawn, the mouthpiece 14, the cartridge 22 (but preferably not the control system 60, which is designed to remain uncontaminated and would be relatively expensive to replace after each use) and the syringe 80 may be disposed of according to conventional waste disposition procedures, and the collected condensate may be taken to a suitable analyzer for analysis.

Because of the relatively small quantities of liquid condensate that may typically be collected using devices 10 of the present invention, it may be useful to include specialized features in the piston 98 and other components in order to maximize the amount of condensate that may be collected. For example, although not absolutely necessary, the piston 98 shown in the various illustrations includes a tip or protrusion 99 of dimensions and shape suitable for fitting snugly into the nipple-shaped inlet 86 when the plunger assembly 84 is fully depressed. This helps to ensure that as much condensate as possible is forced out of the inlet 86. In addition, however, the protrusion 99 may, for example, include grooves, tunnels, or the like for guiding condensate from the condensing chamber 82 to the inlet 86 and out. Specialized pistons 98 such as these are more fully described in the aforementioned U.S. Provisional Patent Application No. 60/434,916.

The analysis of the collected condensate may be carried out using any conventional analysis technique or system. The analysis may focus on identifying and quantifying the presence of a variety of markers of various respiratory diseases. The markers may include microbes such as viruses, fungi, mycoplasma, mycobacteria, bacteria, prions and protozoa, and biochemicals such as inorganic gases, volatile organic molecules, proteins, nucleic acids, lipids, lipid A, endotoxin and other impervious nonorganic exogenous materials such as inhaled particulate including asbestos, silicates, coal dust and the like. These markers and the analysis techniques and systems are well known to those of ordinary skill in the art. Once the analysis is complete, however, a more accurate diagnosis may be made by taking into account the exhalation cycle phase or phases in which the markers were found.

Figure 21:
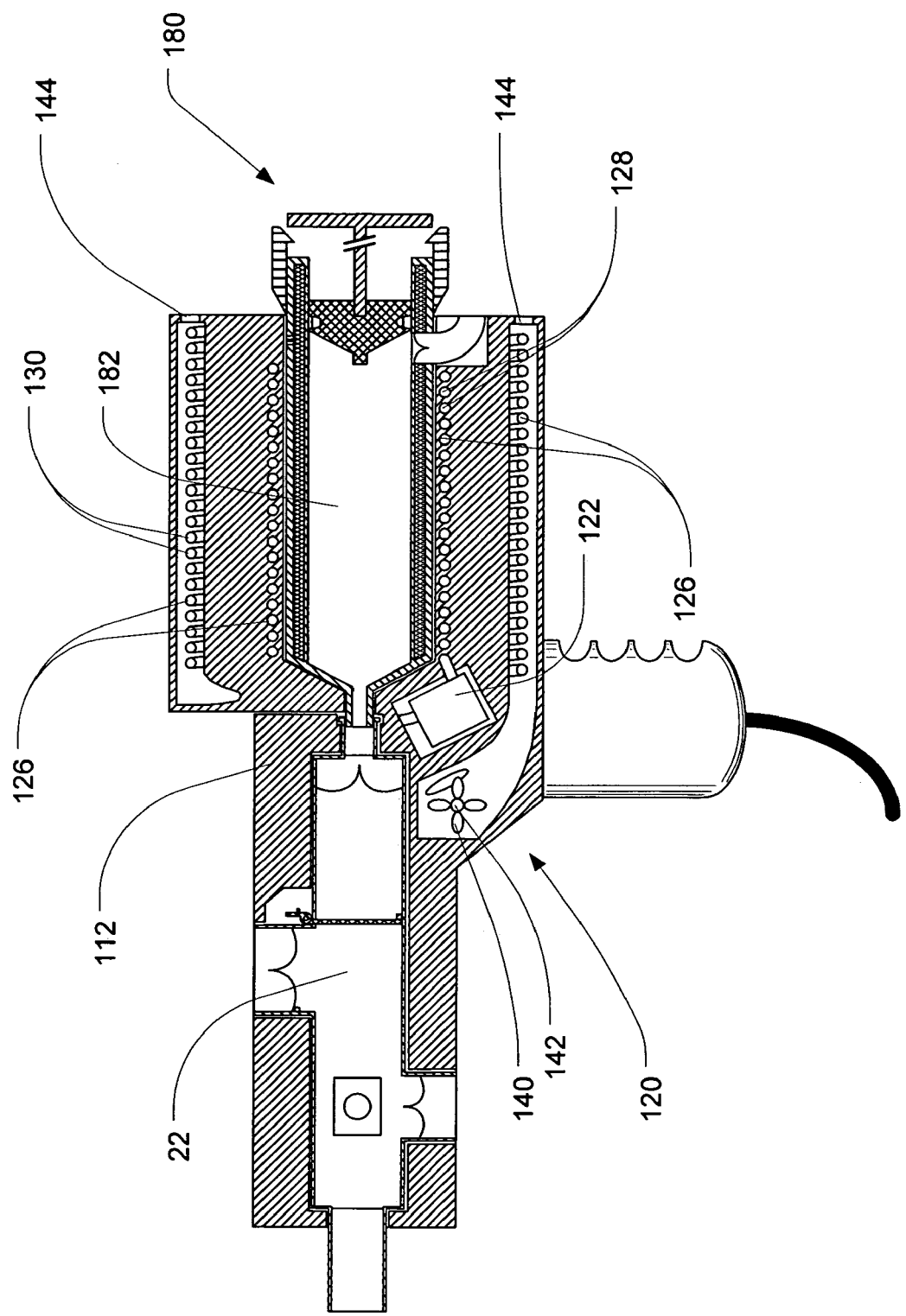
FIG. 21 is a side cross-sectional view of a device for collection of exhaled alveolar breath condensate in accordance with a second preferred embodiment of the present invention.

FIG. 21 is a side cross-sectional view of a device 110 for collection of exhaled alveolar breath condensate in accordance with a second preferred embodiment of the present invention. In this alternative embodiment preferred for its completely self-contained nature, the device 110 includes a refrigeration system 120 built into its housing 112. The refrigeration system 120 is generally of conventional design and includes a compressor 122, an expansion valve (not shown), a distribution system 126 and an exhaust system 140. However, it should be apparent that other types of cooling systems may likewise be utilized without departing from the scope of the present invention. For example, instead of a conventional refrigeration system 120, the alternative device 110 may utilize a cooling jacket comprised of a layer of a liquid having a very low freezing point, such as PEG, in a bag made of rubber or the like, or may use an electric cooler making use of the thermoelectric effect, or other cooling methodologies.

The device 110 may utilize an alternative syringe 180 having a single-walled condensing chamber 182 and a plunger assembly and other features as described herein. The distribution system 126 is a piping or tubing structure having a evaporator (cold) pipe or coil 128 and a condenser (hot) coil 130. The evaporator coil 128 surrounds the recess into which the condensing chamber 182 is inserted. Although not shown herein, the evaporator coil 128 may even make direct contact with the wall of the condensing chamber 182. Preferably, the walls of the condensing chamber 182 are formed of aluminum or another good heat conducting material, thus permitting the refrigeration system 120 to rapidly cool the condensing chamber 182, thus facilitating breath condensate collection within seconds of inserting the syringe 180 therein.

The condenser coil 130 may be cooled using convection cooling via the exhaust system 140, which may include fans 142 and vents 144 such as those shown in the side and end, respectively, of the housing 112 in FIG. 21. The exhausted heat should preferably be directed away from the patient. The compressor 122 may operate using standard 110 volt electrical power or using power supplied by a suitable battery pack. A temperature gauge (not shown) may be provided to indicate when the temperature of the condensing chamber 182 has been lowered sufficiently to allow breath condensation to occur with adequate efficiency, which may be important if the device 110 has not been used for an extended period of time.

Figure 22:
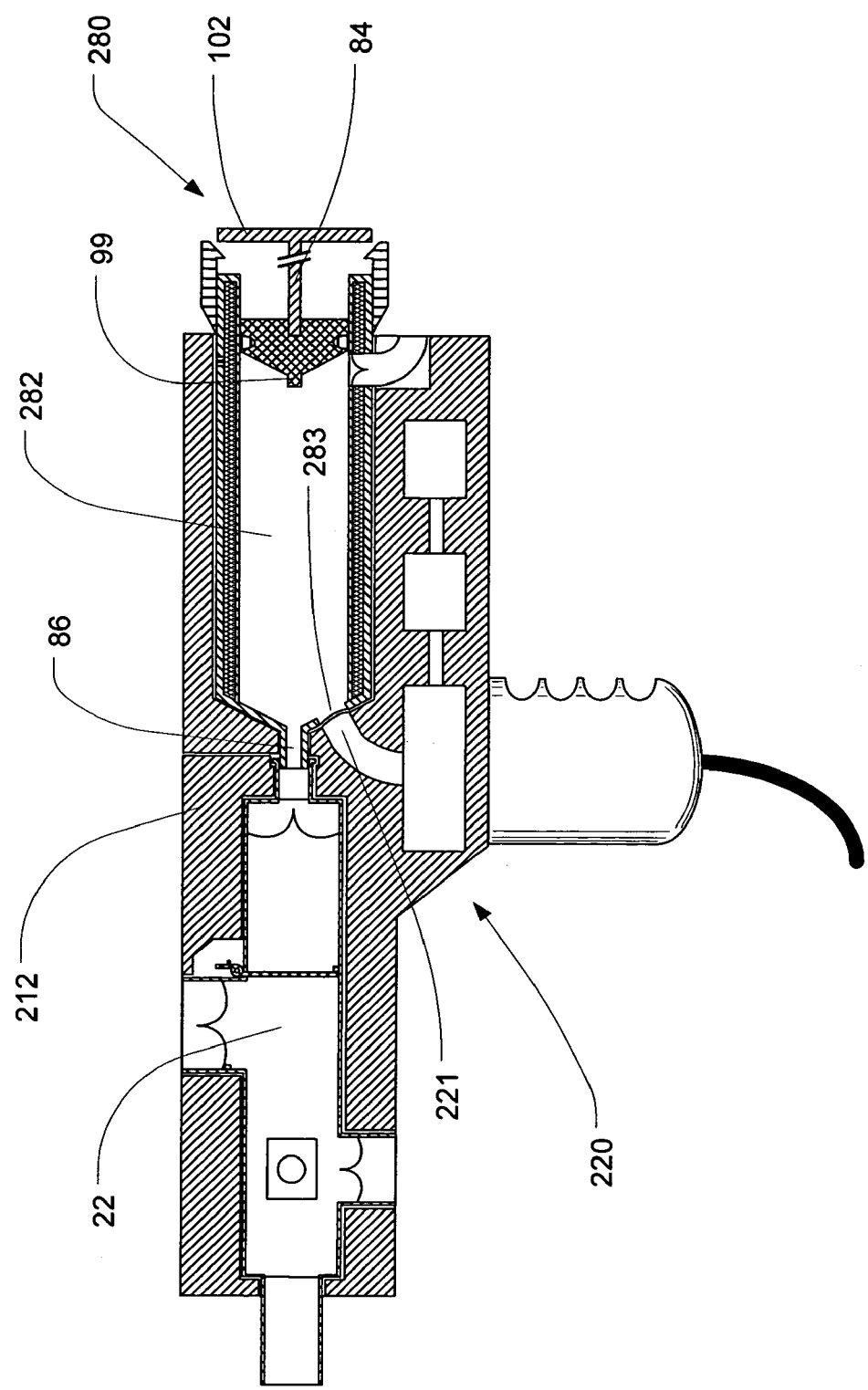
FIG. 22 is a side cross-sectional view of a device for collection of exhaled alveolar breath condensate in accordance with a third preferred embodiment of the present invention.

FIG. 22 is a side cross-sectional view of a device 210 for collection of exhaled alveolar breath condensate in accordance with a third preferred embodiment of the present invention. In this alternative embodiment preferred for its still greater functionality and convenience, the device 210 includes a built-in breath condensate analyzer 220. The built-in analyzer feature may be combined with the built-in refrigeration system 120 described above, or may be utilized separately. In order to deliver the collected condensate to the analyzer 220, a syringe 280 having a special condensing chamber 282 may be utilized. The condensing chamber 282 differs from previously-described condensing chambers 82, 182 in that it includes a small side port 283 extending radially from the entry end of the condensing chamber 282. This permits collected condensate to be expressed directly into the analyzer 220. In addition, it should be noted that the plunger assembly 84 must include a tip or protrusion 99 of a type described previously (or a similar structure) in order to completely plug the nipple-shaped inlet 86 of the condensing chamber 282, thereby preventing condensate from passing back into the cartridge 22 when the plunger assembly 84 is depressed.

Figure 23:
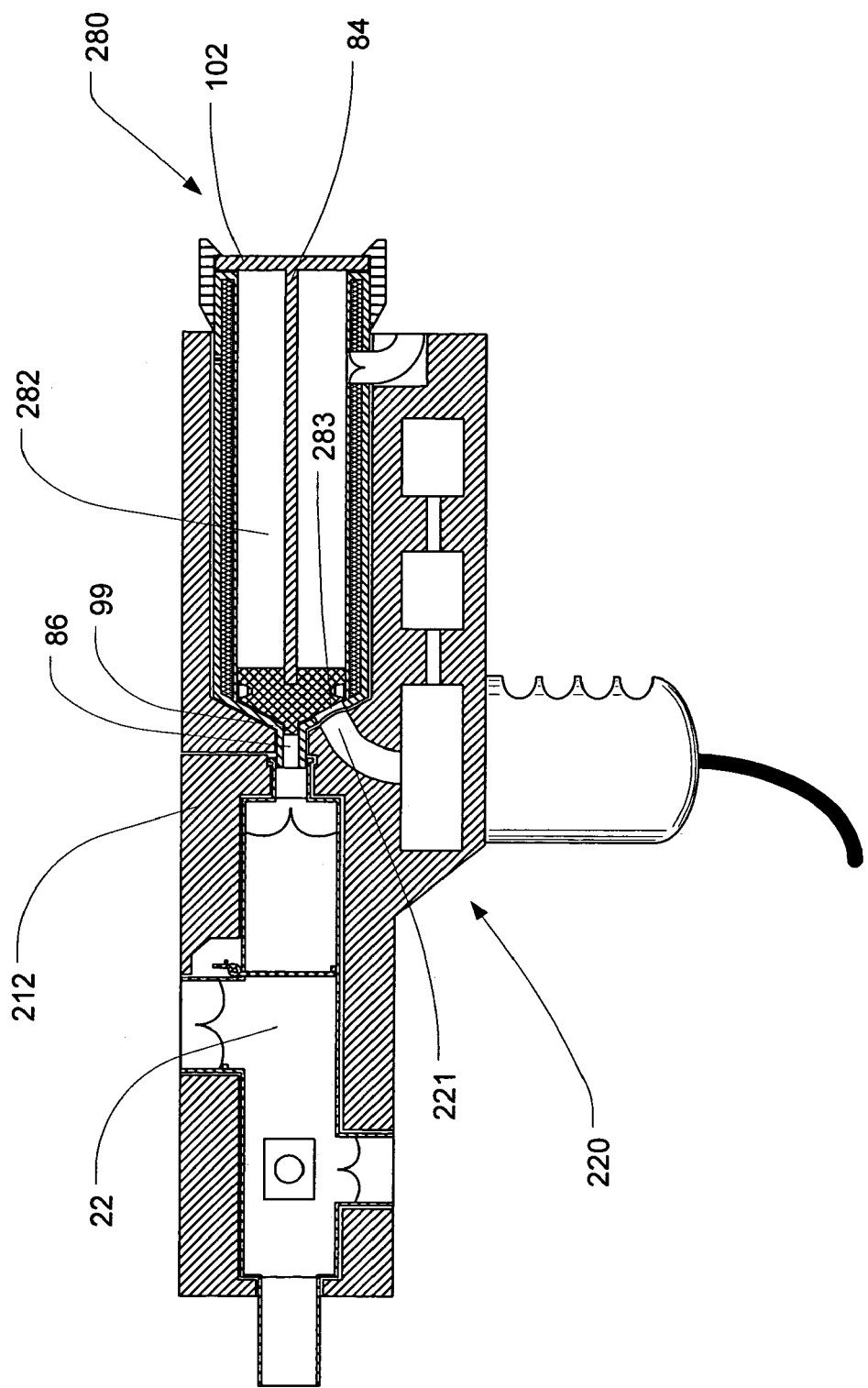
FIG. 23 is a side cross-sectional view of the device of FIG. 22 showing the plunger assembly in a fully inserted position.

In use, a syringe 280 is first inserted into the housing 212 of the device 210. A groove or channel may be provided in the recess of the housing 212 in order to guide the side port 283 into fluid communication with an inlet 221 for the analyzer 220. If the device 210 is equipped with a built-in refrigeration system 120 as described previously, then the condensing chamber 282 may be cooled once it is in place in the housing 112; otherwise, the condensing chamber 282 should be cooled ahead of time. Condensate is then collected in a similar manner to that described hereinabove. When sufficient condensate has been collected, the plunger assembly 84 may be depressed until the plunger handle 102 snaps into place. FIG. 23 is a side cross-sectional view of the device of FIG. 22 showing the plunger assembly 84 in a fully inserted position. This forces the analyte out of the side port 283 and into the analyzer 220, which may include an analysis matrix, such as an immunoassay screen, or permits it to be aspirated by vacuum into an analysis chamber contained within the housing 212 of the device 210.

Figure 24:
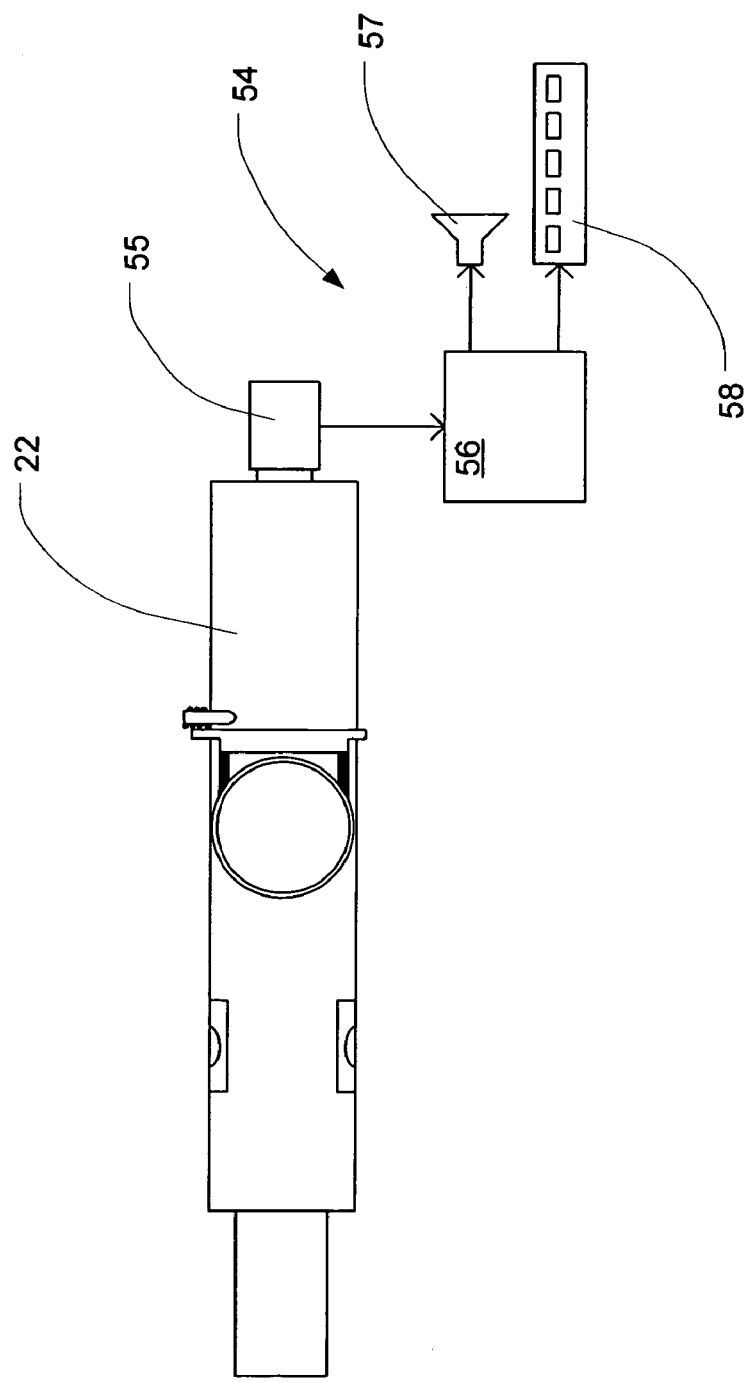
FIG. 24 is a schematic view of an auxiliary control system for use with the device of FIGS. 1, 21 and 22.

FIG. 24 is a schematic view of an auxiliary control system 54 for use with the devices 10, 110, 210 of FIGS. 1, 21 and 22. The auxiliary control system 54 includes a flow transducer 55, a microcontroller or other computer device or electronic logic module 56, and one or more signaling devices 57, 58. The flow transducer 55 may be installed anywhere along the flow path extending from the directional flap 36 in the cartridge 22 to the exhaust port 88 of the respective syringe 80, 180. 280 but is preferably installed at the collection port 30 of the cartridge 22. The microcontroller 56 is interconnected between the flow transducer 55 and the signaling devices 57, 58.

In operation, the flow transducer 55 measures the exhaled alveolar volume passing through the collection port 30 of the cartridge 22 and generates a corresponding analog signal that is monitored by the microcontroller 56. The exhaled alveolar volume that is required in order to produce the volume of condensate needed for accurate chemical analyses can be preprogrammed, based upon experimental analysis, into the microcontroller 56. When the microcontroller 56 determines that that volume has been reached, it transmits a suitable electronic signal to the signaling devices 57, 58, which may include a speaker, one or more LED's or other visual signal devices, or the like. Thus, when the speaker 57 sounds or the LED's 58 light, the operator of the respective device 10, 110, 210 is notified that the breath collection process has been completed. Alternatively, the microcontroller 56 may utilize a more complex signaling pattern, wherein the audible signal emitted by the speaker 57 rises in pitch or in intensity as the process progresses, or a series of LED's 58 are sequentially lit as the process progresses. This approach allows the patient and operator to know how much more breathing is required to complete condensation collection, which may be particularly advantageous for breath collection from children.

It should be apparent that the devices 10, 110, 210 of various embodiments of the present invention may also be used to capture expired breath from the expired airway phase, rather than the alveolar phase, merely by reversing the triggering point for the solenoid 70. This may be accomplished by calibrating the rotary solenoid 70 and the amplifier/differentiator 68 such that the directional flap 36 is initially held in its active state, wherein the flap 36 is held in its open position by the solenoid 70. Alternatively, the spring 50 or other biasing means may be adjusted to bias the directional flap 36 in its open position, and the control system 60 may be adjusted such that when the solenoid 70 is activated, the flap 36 is closed.

The operation of this variation is as follows. As described previously, at the beginning of an expiration by the patient, the patient's breath is dilute in carbon dioxide and rich in oxygen. Thus, when the flap 36 is open, the airway deadspace and associated water content are directed selectively to the syringe 80. As the patient's alveoli begin to empty during expiration, the partial pressure of $CO_2$ increases and the partial pressure of oxygen decreases. The resulting signal generated by the amplifier/differentiator 68 eventually deactivates the solenoid 70, causing the directional flap 36 to close. At this point, the alveolar gas is shunted out the exhaust vent 32 to the environment. The threshold concentration value for $CO_2$ is preferably set at approximately 4 torr, so that once the concentration of $CO_2$ exceeds that value, the actuator device 70 closes the flap 36, thus preventing further exhaled breath from passing into the syringe 80.

Thus, this alternative arrangement may be used to provide specific separation of the expired airway phase from the alveolar phase. More specifically, this would allow selective spectrophotometric measurement of expired concentrations of inorganic gases and volatile organic compounds, as well as collection of expired condensate derived only from the airway phase of exhalation. Then, the condensing chamber 82 could be replaced and the triggering mechanism could be reset to alveolar collection mode, and the process repeated. Because the condensate collected during alveolar collection mode would be from the same subject as that collected during the expired airway mode, the cartridge 22 would not necessarily need to be replaced when changing modes; however, the cartridge 22 may likewise be replaced, if desired, in order to avoid contaminating the condensate collected in one mode with any residual condensate or remaining fluids still present in the cartridge 22 after operation in the first mode.

The advantage of this differential sample collection would be the distinction of pathological processes affecting the lining of the bronchial tree versus processes primarily affecting the alveoli. The ability to distinguish lower airway disease (e.g., on the basis of differential measurement of inflammatory markers) from diseases affecting the conducting tract can have important ramifications on treatment.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A method of collecting breath condensate from a portion of exhaled breath from a mammalian subject by separating the expired airway phase of the breath from the alveolar phase, the method comprising:

providing a cartridge assembly and a condensing chamber, the cartridge assembly having a breathing port and at least two fluid outlets, wherein at least one fluid outlet is in fluid communication with the condensing chamber;

cooling the condensing chamber to a temperature of less than 0° F.;

receiving, at the breathing port in the cartridge assembly, at least one exhaled breath from a mammalian subject;

monitoring, in the cartridge assembly, at least one characteristic of the exhaled breath, the characteristic generally capable of distinguishing the expired airway phase of the breath from the alveolar phase of the breath;

based on the state of the monitored characteristic, diverting the flow of the exhaled breath through the cartridge assembly from one fluid outlet to the other fluid outlet; and upon receiving a diverted portion of the exhaled breath from the cartridge assembly, condensing portions of the exhaled breath to produce condensate on the inner surfaces of the condensing chamber; wherein monitoring includes determining when the exhaled breath has transitioned from the expired airway phase to the alveolar phase, and wherein diverting the flow of the exhaled breath based on the state of the monitored characteristic includes diverting the exhaled breath to the condensing chamber once it is determined that the alveolar phase of the exhaled breath has begun and wherein the monitoring, diverting and condensing steps are repeated in order to increase the amount of condensate produced in the condensing chamber until a predetermined volume of gas has passed into the condensing chamber.

2. A method of collecting breath condensate from a portion of exhaled breath from a mammalian subject by separating the expired airway phase of the breath from the alveolar phase, the method comprising:

providing a cartridge assembly and a condensing chamber, the cartridge assembly having a breathing port and at least two fluid outlets, wherein at least one fluid outlet is in fluid communication with the condensing chamber;

cooling the condensing chamber;

receiving, at the breathing port in the cartridge assembly, at least one exhaled breath from a mammalian subject;

monitoring, in the cartridge assembly, at least one characteristic of the exhaled breath, the characteristic generally capable of distinguishing the expired airway phase of the breath from the alveolar phase of the breath;

based on the state of the monitored characteristic, diverting the flow of the exhaled breath through the cartridge assembly from one fluid outlet to the other fluid outlet; and upon receiving a diverted portion of the exhaled breath from the cartridge assembly, condensing portions of the exhaled breath to produce condensate on the inner surfaces of the condensing chamber;

wherein monitoring includes determining when the exhaled breath has transitioned from the expired airway phase to the alveolar phase, and wherein diverting the flow of the exhaled breath based on the state of the monitored characteristic includes diverting the exhaled breath to the condensing chamber until it is determined that the alveolar phase of the exhaled breath has begun.

3. The method of claim 2, wherein the monitoring and diverting steps are carried out automatically.

4. A breath condensate collection apparatus comprising:

(a) a cartridge assembly including:

a breathing port adapted to permit a mammalian subject to breathe in and out of the cartridge assembly, at least a first fluid outlet and a second fluid outlet, a monitoring system adapted to monitor at least one characteristic of a generally gaseous fluid passing through the cartridge assembly, the at least one characteristic generally capable of distinguishing the expired airway phase of an exhaled breath from the mammalian subject from the alveolar phase of the exhaled breath, and a valve assembly operable to divert the flow of fluid, received via the breathing port, to either the first fluid outlet or the second fluid outlet on the basis of the state of the monitored characteristic; and (b) a condensing chamber having double side walls and first and second opposing ends, wherein the double side walls include an inner side wall and an outer side wall in spaced relationship to one another, wherein the condensing chamber is in fluid communication with at least one fluid outlet of the cartridge assembly and wherein the condensing chamber includes an outlet and a one-way valve adapted to prevent gas from being drawn into the condensing chamber during an inhalation by the mammalian subject while permitting exhaled breath to be exhausted therethrough during an exhalation by the mammalian subject; and wherein an actuator device operates the valve assembly to divert the flow of fluid, received via the breathing port, to the second fluid outlet instead of to the first fluid outlet when a predetermined level of a particular predetermined gas is reached and diverted away from the fluid outlet connected to the condensing chamber when the predetermined level of the particular predetermined gas is reached.

5. The method of claim 1, further comprising expressing the condensate from the condensing chamber using a piston assembly.

6. The method of claim 2, further comprising expressing the condensate from the condensing chamber using a piston assembly.

* * * * *